(12) United States Patent
Sayeh et al.

(10) Patent No.: US 9,406,411 B2
(45) Date of Patent: Aug. 2, 2016

(54) AUTOMATIC CALIBRATION FOR DEVICE WITH CONTROLLED MOTION RANGE

(75) Inventors: Sohail Sayeh, San Ramon, CA (US);
George Asmerom, San Jose, CA (US);
Sankaralingam Ramraj, Sunnyvale, CA (US); Jian Gao, San Jose, CA (US);
Gopinath Kuduvalli, San Jose, CA (US)

(73) Assignee: Accuray Incorporated, Sunnyvale, CA (US)

(*) Notice: Subject to any disclaimer, the term of this patent is extended or adjusted under 35 U.S.C. 154(b) by 1317 days.

(21) Appl. No.: 13/184,370

(22) Filed: Jul. 15, 2011

(65) Prior Publication Data
US 2012/0203490 A1 Aug. 9, 2012

Related U.S. Application Data

(60) Provisional application No. 61/440,813, filed on Feb. 8, 2011.

(51) Int. Cl.
| | | |
|---|---|---|
| G06F 1/16 | (2006.01) | |
| G06F 1/22 | (2006.01) | |
| G01B 3/02 | (2006.01) | |
| G01B 3/10 | (2006.01) | |
| G21K 1/04 | (2006.01) | |
| A61N 5/10 | (2006.01) | |

(52) U.S. Cl.
CPC ............ *G21K 1/04* (2013.01); *A61N 5/1045* (2013.01); *A61N 5/1075* (2013.01)

(58) Field of Classification Search
CPC ...................................................... G06F 19/00
USPC .......................... 702/105; 378/150; 356/511
See application file for complete search history.

(56) References Cited

U.S. PATENT DOCUMENTS

| | | | |
|---|---|---|---|
| 2,675,486 A | 4/1954 | Green | |
| 4,450,578 A | 5/1984 | Hill | |
| 4,476,629 A * | 10/1984 | Suzuki | ............ H01B 13/01245 29/564.4 |

(Continued)

FOREIGN PATENT DOCUMENTS

| | | |
|---|---|---|
| DE | 10 37 035 | 8/1958 |
| DE | 15 64 765 | 1/1970 |

(Continued)

OTHER PUBLICATIONS

PCT Patent Application PCT/EP05/008659 (published as WO 06/119796 on Nov. 16, 2006) International Search Report dated Mar. 21, 2006.

(Continued)

*Primary Examiner* — Gregory J Toatley
*Assistant Examiner* — Felix Suarez
(74) *Attorney, Agent, or Firm* — Lowenstein Sandler LLP

(57) ABSTRACT

An apparatus includes a portion that moves along a guided path and a displacement gauge that outputs readings based on the portion's position on the guided path. The apparatus additionally includes an intermediate limit switch that is activated in response to the portion being moved to an intermediate position on the guided path. The apparatus also includes a processing device configured to calibrate the apparatus based on a first reading corresponding to a first position on the guided path and a second reading corresponding to a second position on the guided path. The processing device verifies the calibration based on a third reading corresponding to the intermediate position.

13 Claims, 17 Drawing Sheets

(56) References Cited

U.S. PATENT DOCUMENTS

| | | | |
|---|---|---|---|
| 4,912,468 A | 3/1990 | Rust | |
| 4,998,268 A | 3/1991 | Winter | |
| 5,274,328 A * | 12/1993 | Begin et al. | 324/207.12 |
| 5,680,434 A | 10/1997 | Thelosen | |
| 5,748,703 A | 5/1998 | Cosman | |
| 5,789,661 A * | 8/1998 | Fauque et al. | 73/37.5 |
| 5,805,291 A * | 9/1998 | Calvin | G01B 11/0691 250/559.12 |
| 5,991,362 A | 11/1999 | Jones | |
| 5,992,223 A * | 11/1999 | Sabins et al. | 73/64.42 |
| 6,052,430 A | 4/2000 | Siochi | |
| 6,067,165 A * | 5/2000 | Matsumiya et al. | 356/401 |
| 6,136,274 A | 10/2000 | Nova et al. | |
| 6,227,940 B1 * | 5/2001 | Bartlett | B23Q 11/08 451/10 |
| 7,132,674 B2 | 11/2006 | Pastyr | |
| 7,619,746 B2 * | 11/2009 | De Lega | 356/511 |
| 8,373,852 B2 * | 2/2013 | Ruchet et al. | 356/73.1 |
| 2004/0251340 A1 * | 12/2004 | Tavares et al. | 241/34 |
| 2005/0137751 A1 | 6/2005 | Cox et al. | |
| 2005/0224727 A1 | 10/2005 | Papaioannou | |
| 2006/0274925 A1 | 12/2006 | West | |
| 2008/0013687 A1 | 1/2008 | Maurer | |
| 2008/0123813 A1 | 5/2008 | Maurer | |
| 2008/0130825 A1 | 6/2008 | Fu | |
| 2009/0001296 A1 | 1/2009 | Kuduvalli | |
| 2009/0074148 A1 | 3/2009 | Echner | |
| 2009/0220046 A1 | 9/2009 | Ji et al. | |

FOREIGN PATENT DOCUMENTS

| | | |
|---|---|---|
| EP | 0 382 560 | 8/1990 |
| EP | 1 367 604 | 12/2003 |
| EP | 1 454 653 | 9/2004 |
| EP | 1 720 173 | 5/2005 |
| FR | 2 113 337 | 6/1972 |
| FR | 1 605 155 | 3/1973 |
| FR | 2 524 690 | 10/1983 |
| JP | 04072880 | 3/1992 |
| JP | 07047142 | 2/1995 |
| JP | 2004267250 | 9/2004 |
| WO | WO 2006-119796 | 11/2006 |

OTHER PUBLICATIONS

European Patent Application No. 05009871.4 (published as EP1720173 on Nov. 8, 2006), European Search Report Dated Oct. 21, 2005.

International Search Report and Written Opinion mailed Sep. 19, 2012, for PCT Application No. PCT/US2012/024016, filed Feb. 6, 2012, 24 pages.

"Intermediate Sensor", IBM Technical Disclosure Bulletin, International Business Machines Corp. (Thornwood), US, vol. 36, No. 11, Nov. 1, 1993, p. 647/648, XP000424979, ISSN: 0018-8689.

* cited by examiner

AUTOMATIC CALIBRATION FOR DEVICE WITH CONTROLLED MOTION RANGE

RELATED APPLICATIONS

This patent application claims the benefit under 35 U.S.C. §119(e) of U.S. Provisional Application No. 61/440,813, filed Feb. 8, 2011, which is herein incorporated by reference.

TECHNICAL FIELD

Embodiments of the present invention relate to instrument calibration and, in particular, to a self calibrating device.

BACKGROUND

Collimators are frequently used in radiation treatment for narrowing a beam of highly energized particles, referred to as a treatment beam. Some radiation treatment systems use a variable aperture collimator called a multi-leaf collimator (MLC). A multi-leaf collimator is a collimator that is made up of a collection of individual leaves that can move independently in and out of the path of the treatment beam. For conformal radiotherapy, the MLC enables conformal shaping of the treatment beam to match borders of a target. In the MLC, each leaf is powered by its own motor, and has its own displacement gauge to precisely control the position of the leaf. To ensure accuracy, each individual displacement gauge of each leaf must be calibrated by a technician. Additionally, MLCs are highly complex, and susceptible to numerous avenues of failure.

Accuray® Incorporated manufactures another type of variable aperture collimator called the IRIS™ Collimator. The IRIS collimator also has multiple leaves. However, the leaves of the IRIS collimator are all driven together by a single motor to enlarge or decrease the aperture size similar to the operation of an iris diaphragm in a camera. As with MLC collimators, the IRIS collimator occasionally needs to be calibrated by a technician.

BRIEF DESCRIPTION OF THE DRAWINGS

The present invention is illustrated by way of example, and not by way of limitation, in the figures of the accompanying drawings.

DETAILED DESCRIPTION

Described herein is a method and apparatus that can be automatically calibrated, such as a self calibrating adjustable aperture collimator used in radiation treatment. In one embodiment, a self calibrating apparatus (e.g., a self calibrating variable aperture collimator) includes a portion (e.g., one or more leaves) that moves along a guided path and a displacement gauge that outputs readings based on the portion's position on the guided path. These readings can be used to measure a position of the portion (e.g., of a leaf). For variable aperture collimators, these readings can be used to calculate an aperture. The apparatus additionally includes a first limit switch that is activated in response to the portion being moved to a first position on the guided path, a second limit switch that is activated in response to the portion being moved to a second position on the guided path, and a third limit switch that is activated in response to the portion being moved to a third position on the guided path that is between the first position and the second position. The apparatus includes a processing device configured to receive, from the displacement gauge, a first reading corresponding to the first position, a second reading corresponding to the second position and a third reading corresponding to the third position. The processing device is further configured to calibrate the apparatus based on the first reading and the second reading, and to verify the calibration based on the third reading.

The ability for an apparatus to self calibrate, and to verify calibration results, provide numerous advantages over prior art systems that require manual calibration. Systems that can self calibrate (as described in embodiments of the present invention) reduce user interaction, and minimize the chance of user error. Additionally, automatic self calibration can be completed more quickly than calibration performed by a user. With the introduction of an automatic calibration verification mechanism (as reflected in embodiments of the present invention), the automatic self calibration may also have a higher accuracy than calibration performed by a user. Embodiments of the present invention may provide calibration accuracy of up to 0.1 mm, depending on component selection.

Figure 1A:
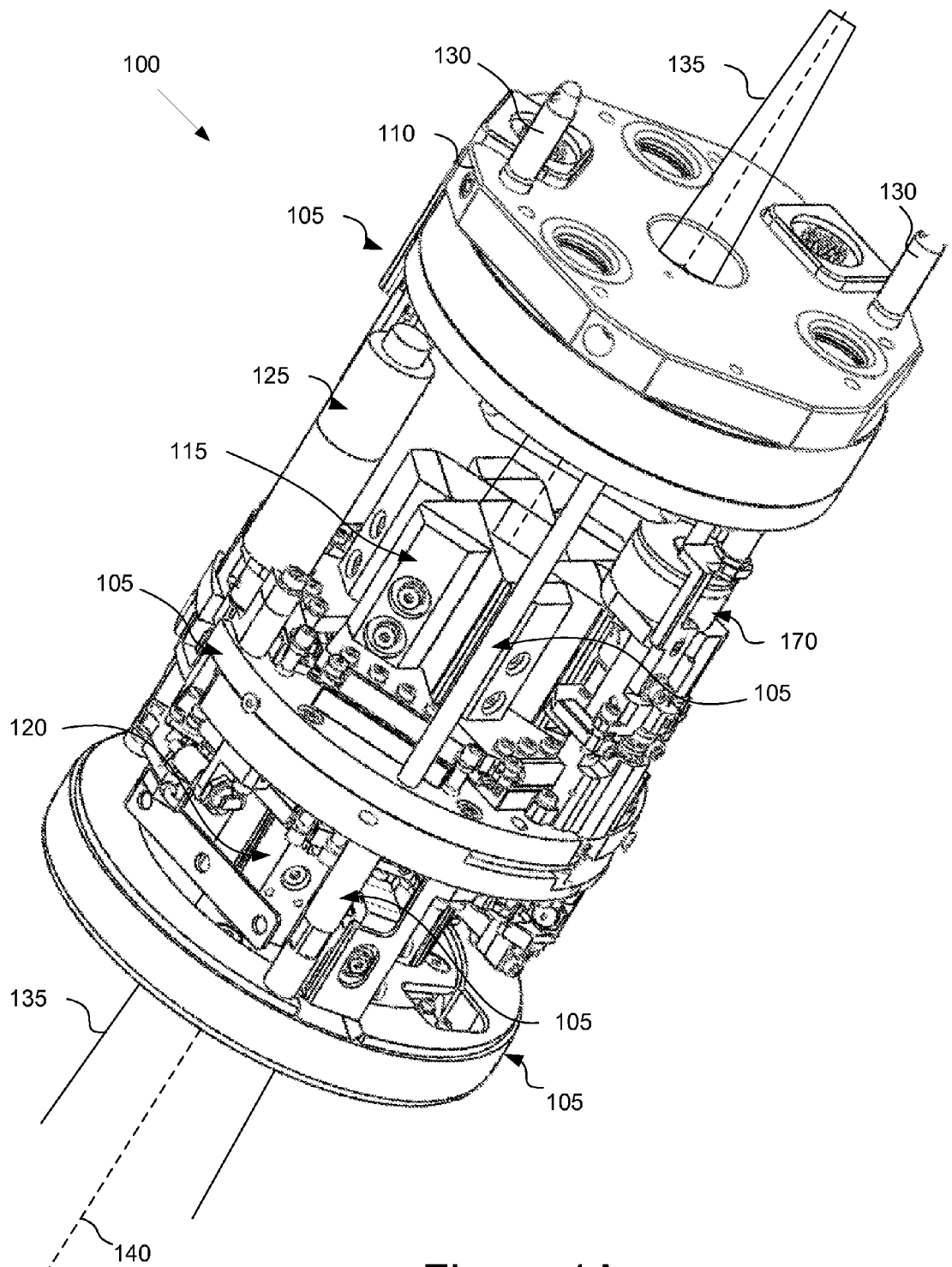
FIG. 1A illustrates an example variable aperture collimator, in accordance with one embodiment of the present invention.

FIG. 1A illustrates an example variable aperture collimator 100 (referred to herein simply as collimator 100 for brevity), in accordance with one embodiment of the present invention. The illustrated variable aperture collimator 100 is an adjustable diaphragm collimator. An adjustable diaphragm collimator is a variable aperture collimator having one or more banks of collimation leaves that move together to change an aperture of the collimator. Another type of variable aperture collimator to which embodiments of the present invention may apply is a multi-leaf collimator (MLC). An MLC has multiple collimation leaves that are independently controllable.

The collimator 100 may be a self calibrating collimator that automatically takes readings and provides the readings to a computing device for processing. The collimator 100 includes a frame assembly 105 on which is mounted a tool plate 110, a top bank 115 of collimation leaves, a bottom bank 120 of collimation leaves, a drive mechanism 125 and a brake mechanism 170.

The collimator 100 mounts to a linear accelerator via the tool plate 110. The tool plate 110 includes guide members 130 to precisely position the collimator 100 with respect to the linear accelerator. The linear accelerator generates a radiation treatment beam 135 that travels through the top bank 115 and the bottom bank 120 of the collimator 100. The radiation treatment beam 135 emerging from the bottom bank 120 is collimated. The radiation treatment beam 135 has an axis of symmetry 140 (corresponding to the center of the treatment beam) that corresponds to a treatment axis of the linear accelerator.

Figure 1B:
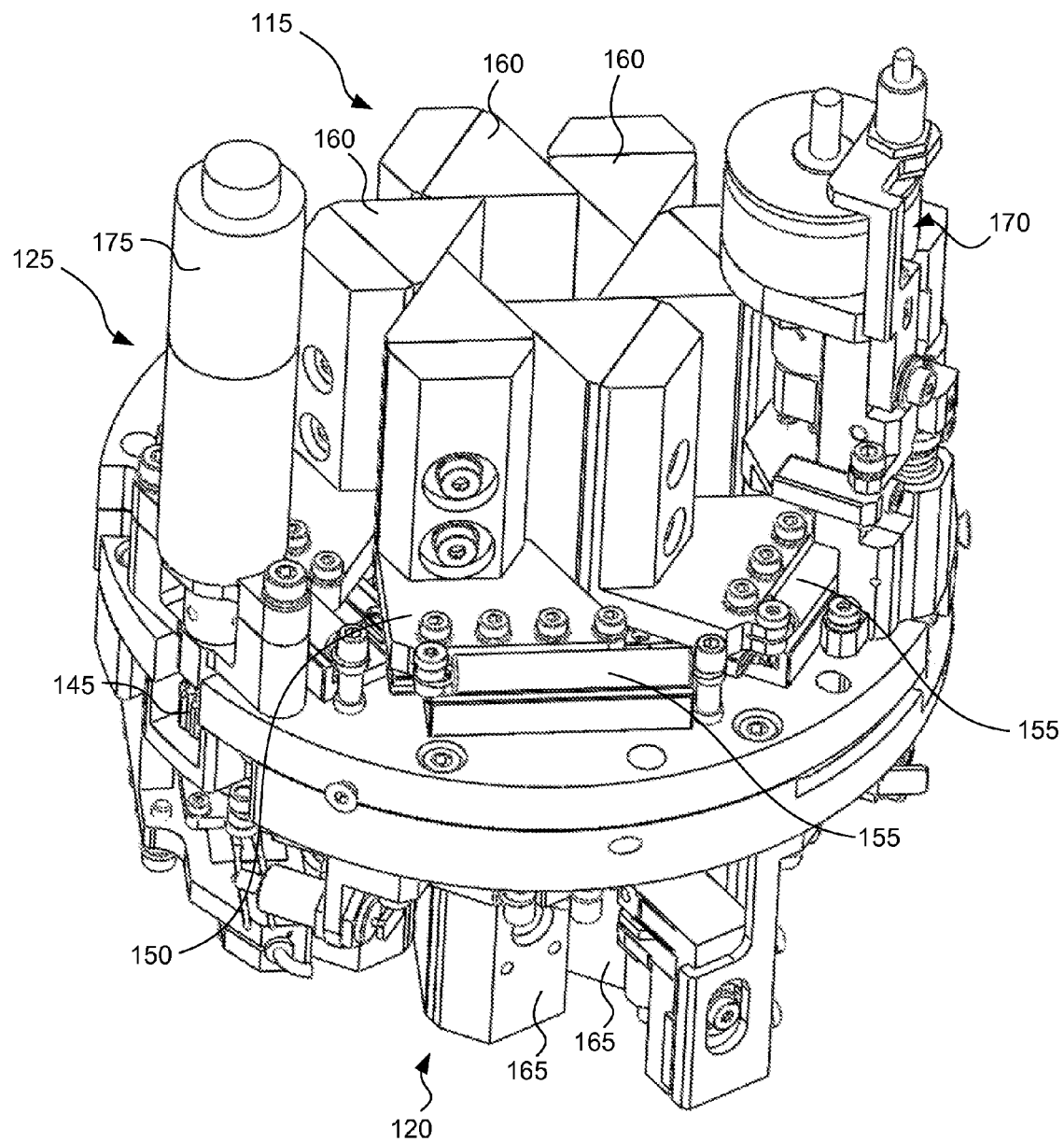
FIG. 1B illustrates a zoomed in view of a variable aperture collimator, showing a top bank of collimation leaves, a bottom bank of collimation leaves, a drive mechanism, and a brake mechanism, in accordance with one embodiment of the present invention.

FIG. 1B illustrates a zoomed in view of the collimator 100, showing the top bank 115 of collimation leaves, the bottom bank 120 of collimation leaves, the drive mechanism 125 and the brake mechanism 170, in accordance with one embodiment of the present invention. As shown in FIG. 1B, the top bank 115 includes a precisely arranged collection of movable collimation leaves 160. Each of the leaves 160 may be manufactured from tungsten or another high density material. Similarly, the bottom bank 120 includes another precisely arranged collection of movable collimation leaves 165, which are mostly hidden from view in FIG. 1B. In one embodiment, the top bank 115 and the bottom bank 120 are coaxial. As the leaves 160, 165 move, the aperture of the collimator 100 changes. In one embodiment, the leaves 160 are arranged so that there is no friction between the leaves 160. In one embodiment, friction is minimized or eliminated by introducing a gap between the leaves 160 (e.g., so that no leaves are touching other leaves). The gap may be, for example, between 25 um to 150 um. Alternatively, other gap sizes may be used. Similarly, the leaves 165 may be arranged so that there are gaps between the leaves 165. Other techniques for reducing or eliminating friction between the leaves may also be used, such as by polishing and/or lubricating the leaves or adding bearings between the leaves.

The drive mechanism 125 includes a motor 175 that drives a gear 145. The gear 145 interlocks with a drive train (not shown) that drives a cam plate (not shown). Each leaf 160, 165 is mounted to a wing 150 that follows a guided path. Each wing 150 interconnects with a cam follower (not shown) that is driven by the cam plate as the motor 175 rotates. In one embodiment, the cam plate and cam follower provide the guided path. Additionally, springs 155 apply force to each wing 150 at all times to reduce or eliminate backlash and/or hysteresis. A brake mechanism 170 applies braking force to prevent the cam plate, wings 150 and leaves 160, 165 from moving when the motor 175 is not being powered.

Figure 2:
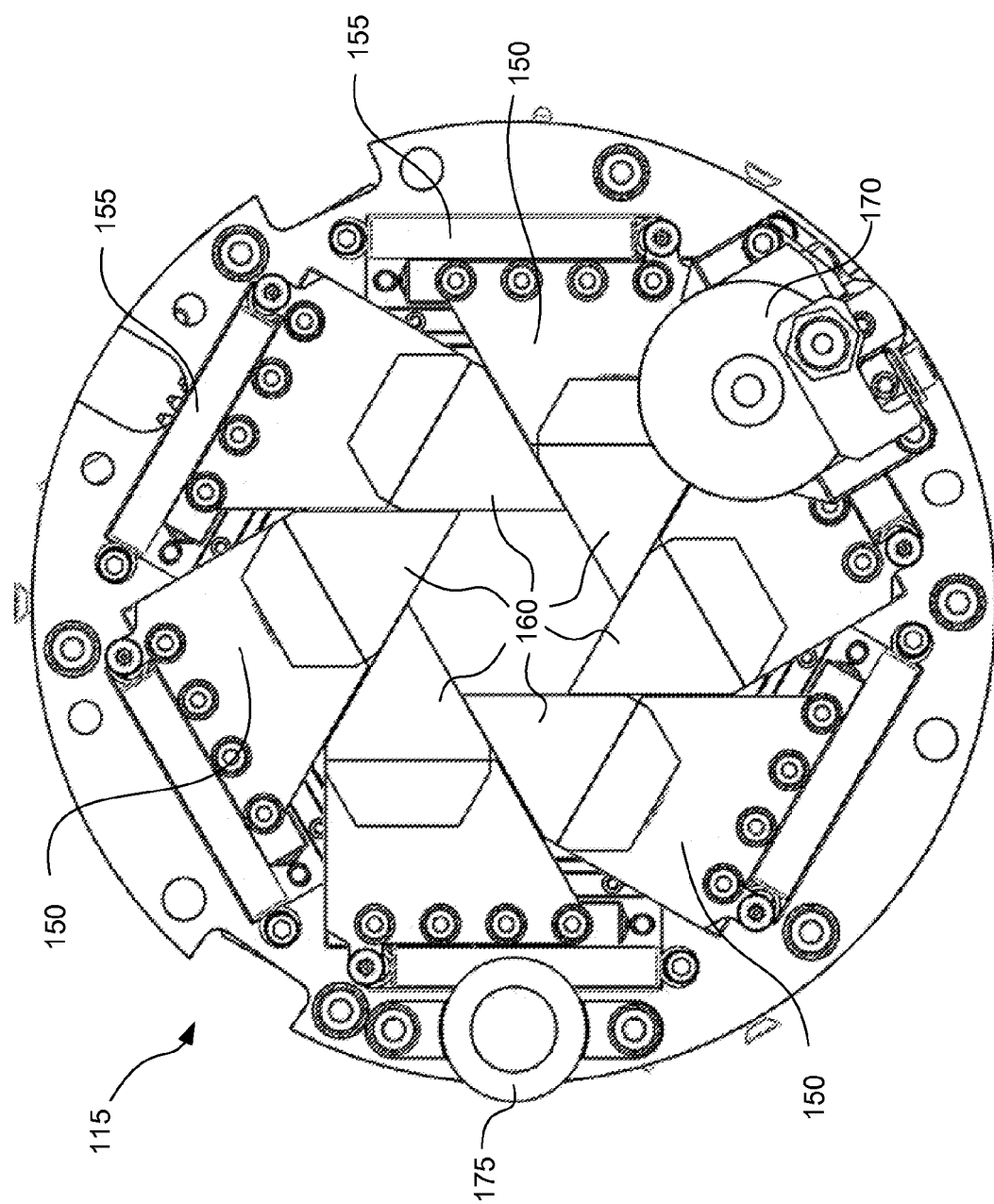
FIG. 2 illustrates a top view of a variable aperture collimator showing a top bank of collimation leaves, in accordance with one embodiment of the present invention.

FIG. 2 illustrates a top view of the collimator 100 showing the top bank 115. As shown, a spring 155 is connected to each wing 150. The spring 155 applies a force to the wing 150 sufficient to overcome any backlash that may be caused by the interface of the cam follower with the cam plate. In one embodiment, all of the springs 155 apply an approximately equal force to the wings 150 to which they are attached. In one embodiment, all springs 155 on the top bank apply a closing force on the leaves 160. Therefore, in the result of a brake and motor failure, the springs 155 will automatically pull the leaves 160 closed, reducing the aperture of the collimator 100 to a minimum and thus minimizing the amount of radiation that might be delivered to a patient. Alternatively, some springs 155 may apply a closing force while other springs apply an opening force.

In one embodiment, all springs 155 connected to wings 150 on the bottom bank 120 also apply a closing force to the leaves 165. In an alternative embodiment, some springs 155 connected to wings 150 in the bottom bank 120 apply a closing force, while other springs 155 connected to wings 150 in the bottom bank 120 apply an opening force. If all springs 155 apply a closing force, then a more powerful motor may be required to overcome the force of the springs 155 and a much larger brake may be required to hold the desired aperture position. However, if some springs 155 apply an opening force, these springs 155 still eliminate backlash and/or hysteresis for the leaves to which they are attached, but reduce the overall force that the motor needs to overcome to drive the leaves 160, 165 open. In one embodiment, all leaves 160 on the top bank 115 are biased closed by the springs 155, while half of the leaves 165 on the bottom bank 120 are biased closed and the other half are biased open. Therefore, the overall biasing force will still cause the banks of leaves to close, but there is reduced force for the motor to overcome to increase the aperture. In one embodiment, every other leaf in the bottom bank is biased closed (springs apply a closing force), with the other leaves being biased open (springs apply an opening force). Therefore, forces applied to the bottom bank 120 are balanced.

As noted, in one embodiment each of the wings 150 (and thus the leaves 160, 165) are driven along a linear path by the motor 175 driving a small pinion gear, which in turn drives gear 145. Gear 145 has slots inside which cam follower rollers attached to the leaf (or a wing associated with the leaf) travel. When gear 145 rotates, driven by the motor 175 and the pinion gear, wings 150 move along the linear slots. This series of mechanical connections between moving parts can potentially add backlash to the variable aperture collimator 100. In one embodiment, the variable aperture collimator 100 includes an encoder that monitors a relative number of turns that the motor 175 has rotated from a given reference point. Separately, a displacement gauge measures linear displacement (and thus aperture). In the presence of backlash, when the motor 175 first attempts to drive the wings 150 from a given position, an initial fraction of the rotation of the motor 175 may be used up in overcoming the backlash. The encoder may count (e.g., fractions of a rotation) until the displacement gauge measures a change. This count may provide a measure of the backlash. By driving the wings 150 (and thus the leaves 160, 165) back and forth from different starting positions of the leaves to destination positions, a model for variable backlash over the entire range of motion of the leaves can be generated. The model may account for direction of movement of the leaves.

Figure 3A:
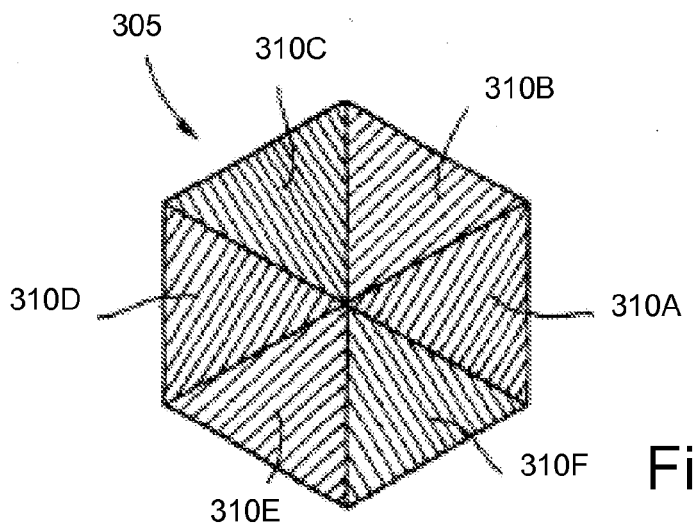
FIGS. 3A-3C illustrates a schematic diagram of a bank of six collimator leaves, in accordance with one embodiment of the present invention.
Figure 3B:
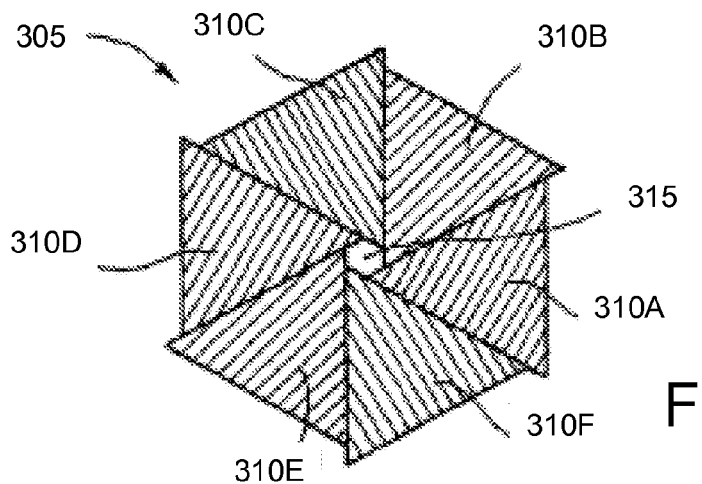
Figure 3C:
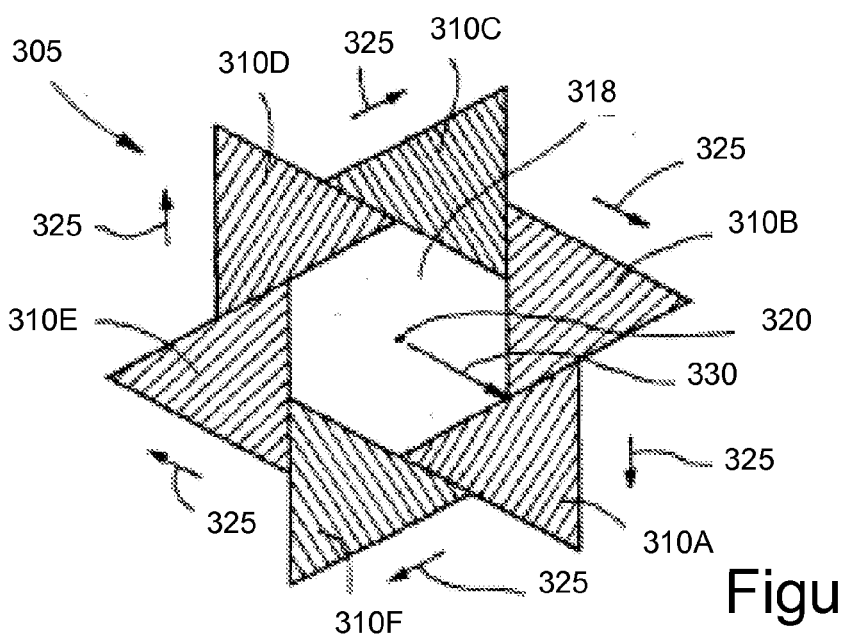

FIGS. 3A-3C illustrate a schematic diagram of a bank 305 of six collimator leaves 310A-310F, showing operation of an adjustable diaphragm collimator, in accordance with one embodiment of the present invention. In one embodiment, the bank 305 corresponds to bank 115 and/or bank 120 of FIGS. 1A-2. The six leaves 310A-310F each move linearly along a guided path (single degree of freedom), with all leaves moving in a plane. The direction of travel of each leaf is shown with arrows 325. By moving each leaf 310A-310F simultaneously (with each leaf 310A-310F moving along its own linear guided path), the aperture of the bank 305 can be adjusted. An arrow 330 shows a distance from the center 320 of the bank 305 to the intersection of two leaves. This distance may define a current aperture of the bank 305. A first aperture 315 is shown in FIG. 3B, and a second larger aperture 318 is shown in FIG. 3C. Each of the leaves 310A-310F may move an equal distance so that the aperture is formed by partial areas of the leaves' side surfaces (each of which may have the same distance from the center 320). Accordingly, in one embodiment, the inner sides of the leaves 310A-310F form a regular polygon (e.g., a regular hexagon when six leaves are used).

Figure 4A:
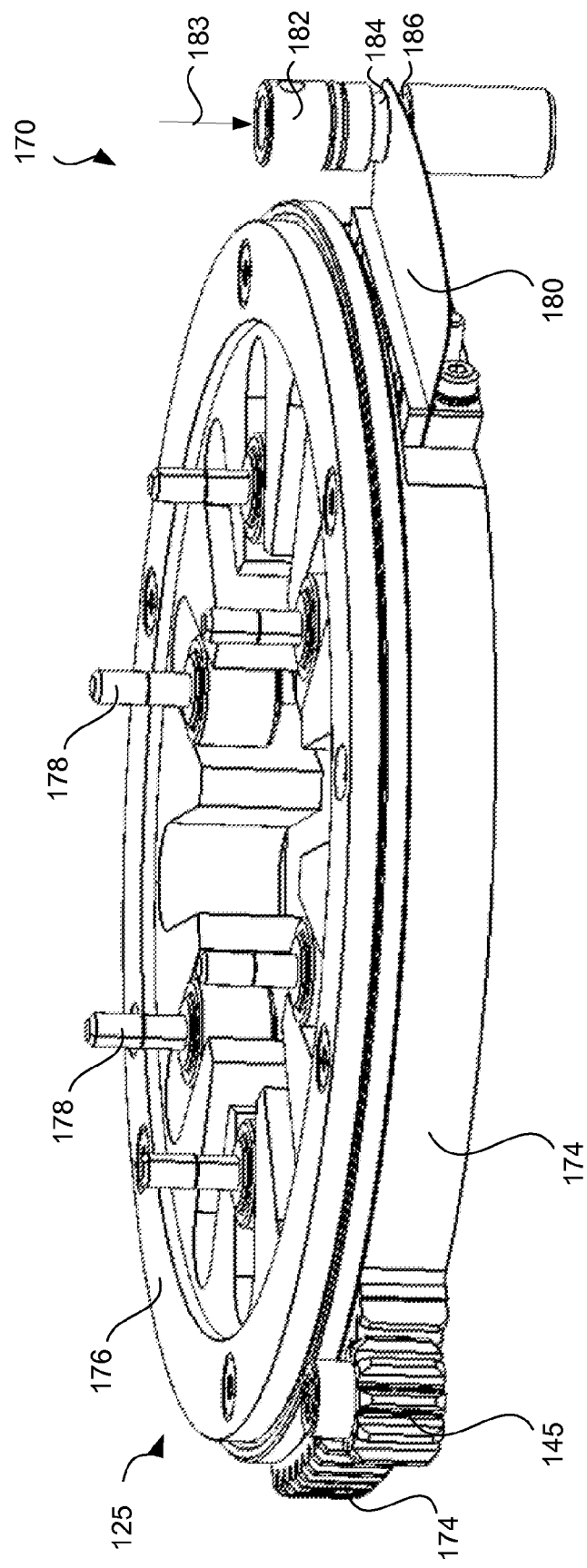
FIGS. 4A-4B illustrate schematic diagrams of a drive mechanism and a brake mechanism for a variable aperture collimator, in accordance with one embodiment of the present invention.
Figure 4B:
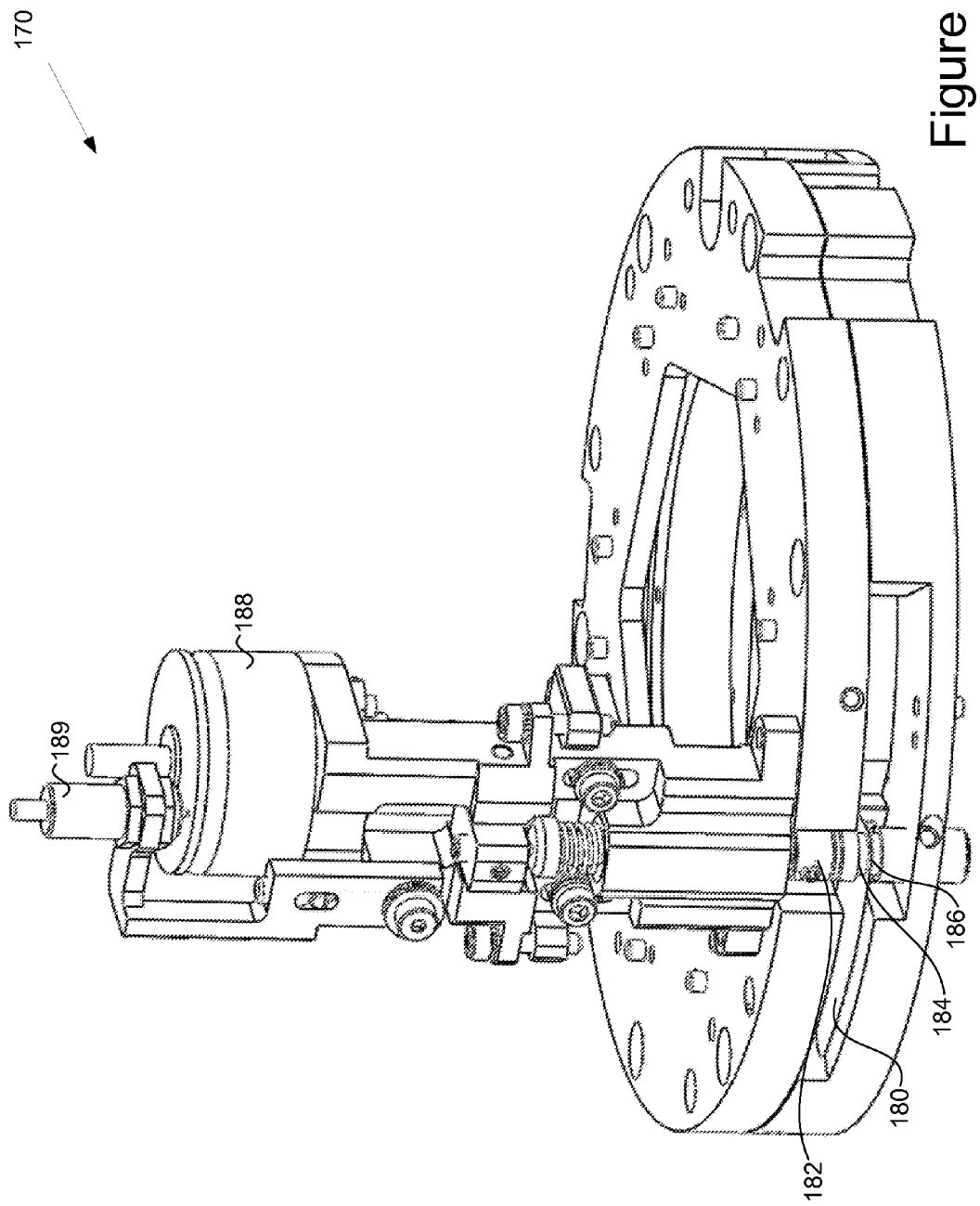

FIGS. 4A-4B illustrate schematic diagrams of the drive mechanism 125 and brake mechanism 170, in accordance with one embodiment of the present invention. The drive mechanism 125 may include a motor 175, gear 145, drive train 174, cam plate 176 and cam followers 178. The brake mechanism 170 may include a solenoid 188, limit switch 189, springs (not shown), plunger 182, brake pads 184, 186 and brake disc 180. A brake disc 180 is attached to the drive train 174. The brake disc 180 is disposed between an upper brake pad 184 and a lower brake pad 186. The brake disc 180 is sized such that a portion of the brake disc 180 is between the upper and lower brake pads 184, 186 at every possible position of the cam plate 176 (and thus of every possible aperture of the collimation leaves 160, 165). In one embodiment, the brake disc 180 is a thin steel, and the brake pads 184, 186 are copper. The brake disc 180 and/or brake pads 184, 186 may be roughened to increase friction. In one embodiment, there is a gap (e.g., of between 0.002 inches to 0.2 inches) between the brake disc 180 and the upper brake pad 184 and lower brake pad 186. In one embodiment, there is a larger gap between the brake disc 180 and the upper brake pad 184 than between the brake disc 180 and the lower brake pad 186.

In one embodiment, the lower brake pad 186 is fixed, and the upper brake pad 184 moves along an axis 183 that is parallel to the treatment axis 140 (as shown in FIG. 1A). Alternatively, both the upper brake pad 184 and lower brake pad 186 may move along the axis 183 in opposing directions by a caliper. A plunger 182 drives the upper brake pad 184 towards the lower brake pad 186 when the brake is engaged. In one embodiment, a constant force exerts pressure on the plunger 182 to engage the brake. The constant force may be exerted, for example, by one or more springs. In one embodiment, the springs cause a constant force of up to 22 lbs. To release (disengage) the brake, power is applied to the brake mechanism 170 to overcome the constant force. Therefore, if any problems occur, the brake automatically engages to stop movement of the collimation leaves 160, 165.

In one embodiment, the plunger 182 includes a spherical joint, so that the upper brake pad 184 can bend in two directions to always meet the angle of the brake disc 180. This increases the contact area between the brake disc 180 and the brake pads 184, 186, thus increasing the braking force. In one embodiment, the spherical joint is a pair of flexures, each flexure being flexible along a single axis that is perpendicular to the axis along which the other flexure is flexible. Instead of, or in addition to, the plunger 182 including a ball joint, the bottom brake pad 186 may be mounted to a spherical joint.

In one embodiment, solenoid 188 applies a force to disengage the brake when power is applied to the solenoid 188. In one embodiment, the solenoid applies a force of approximately 8 lbs., which may be translated into approximately 24 lbs. of force by a 3 to 1 lever arm. In one embodiment, a limit switch 189 is activated when the solenoid is turned on (and thus when the brake is disengaged). The limit switch 189 may thus be used to verify whether the brake is engaged or disengaged. This gives feedback to verify whether the brake is on or off before powering the motor 175.

In one embodiment, the brake disc 180 is flexible in the axis 183 on which the plunger 182 moves (e.g., in the treatment axis) and inflexible in other axes. The flexibility of the brake disc 180 allows the brake disc 180 to bend when the plunger 182 presses the upper brake pad 184 against the lower brake pad 186. This can ensure that no torque or other force will be applied to the cam plate 176 or to any of the leaves or other components. Therefore, engaging the brake does not introduce any unwanted movement into any component of the collimator, and alignment of all components can be maintained even after extensive application of the brake.

When the brake is released, the cam plate 176 is allowed to rotate about its center. The cam plate 176 is rotated by gear 145 rotating and engaging drive train 174. The gear 145 may be precisely rotated by motor 175, which in one embodiment is a DC motor or gear motor. As the cam plate 176 rotates, cam followers 178 move the leaves 160, 165 of the top bank 115 and bottom bank 120. In one embodiment, the collimator 100 includes a single cam plate 176 positioned between the top bank 115 and the bottom bank 120. A single motor 175 may drive the single cam plate 176, which may move all leaves of the top bank 115 and bottom bank 120 simultaneously.

Figure 5:
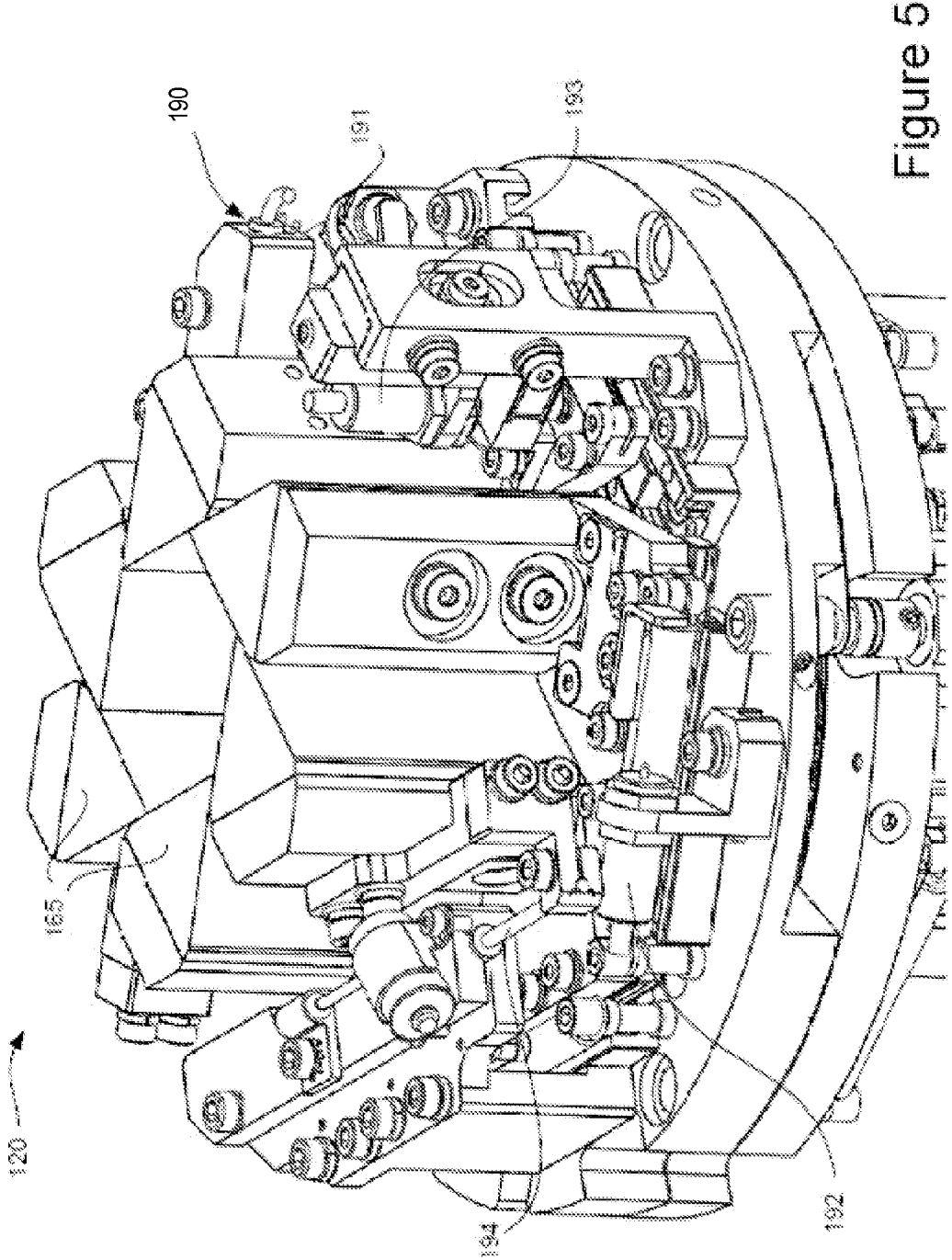
FIG. 5 illustrates a zoomed in view of a variable aperture collimator, showing a bottom bank of collimation leaves and a calibration mechanism, in accordance with one embodiment of the present invention.

FIG. 5 illustrates a zoomed in view of the collimator 100, showing the bottom bank 120 and a calibration mechanism 190, in accordance with one embodiment of the present invention. The calibration mechanism 190 includes a maximum aperture limit switch 191, a minimum aperture limit switch 192, an intermediate aperture limit switch 193 and one or more displacement gauges 194. In one embodiment, the calibration mechanism 190 includes two or more maximum aperture limit switches 191, minimum aperture limit switches 192, intermediate aperture limit switches 193 and displacement gauges 194. This may provide redundancy. In one embodiment, the limit switches 191, 192, 193 are mechanical limit switches. In another embodiment, the limit switches are optical proximity switches or magnetic proximity switches. Alternatively, other types of optical sensors, contact sensors, magnetic sensors or ultrasound sensors may be used instead of a limit switch. In one embodiment, the limit switches are manufactured by Veeder-Root®, part number 748300-003.

When the maximum aperture limit switch 191 is activated, the limit switch 191 generates a signal that indicates the collimator 100 is at its maximum aperture. In one embodiment, the signal causes the motor 140 to stop, so that the motor 140 does not drive the banks 115, 120 past their maximum aperture limits. Similarly, when the minimum aperture switch 192 is activated, the limit switch 192 generates a signal that indicates the collimator 100 is at its minimum aperture. In one embodiment, the signal causes the motor 125 to stop, so that the motor 125 does not drive the banks 115, 120 past their minimum aperture limits. This may prevent damage to the collimator. The third limit switch 193 generates a signal when the leaves 160, 165 of the top bank 115 and bottom bank 120 are at one or more specific positions. This information may be used to verify calibration and/or to generate a non-linear sensor model, as discussed below. In one embodiment, a reading is recorded when the maximum aperture limit switch 191 is activated, then the minimum aperture limit switch 192 is activated, and for each position at which the intermediate aperture limit switch 193 is activated and deactivated.

In one embodiment, the displacement gauge 194 is a linear variable differential transformer (LVDT). One example of an LVDT that may be used is a differential variable reluctance transducer (DVRT) manufactured by MicroStrain®. In another embodiment, the displacement gauge is a rotary variable differential transformer (RVDT). The displacement gauge 194 outputs a reading that is dependent on how far the leaves 160, 165 have moved along their guided paths. In one embodiment, the displacement gauge 194 outputs a voltage whose value is dependent on the leaves' positions. There may be an approximately linear relationship between voltage and displacement.

In one embodiment, the relationship between voltage and displacement is modeled using a linear sensor model. With the linear sensor model, given readings at two known positions, the displacement gauge can be calibrated such that a displacement can be known for any voltage reading of the displacement gauge. If the known positions are aperture values, then the aperture can be known for any voltage readings of the displacement gauge.

In one embodiment, the relationship between voltage and displacement is modeled using a non-linear sensor model. The non-linear sensor model may be more complex than a linear sensor model, but may account for nonlinearities between aperture values and displacement gauge readings. To generate a non-linear sensor model, three or more points are used to model the aperture value to displacement gauge reading responses. These points may include a first sensor reading generated at the minimum aperture limit switch 192, a second sensor reading generated at the maximum aperture limit switch 191, and one or more intermediate sensor readings generated at locations where the intermediate aperture limit switch 193 was activated or deactivated. In one embodiment, curve fitting techniques are applied to sensor readings to generate the non-linear sensor model. Remaining reference points (other points at which the intermediate aperture limit switch 193 is activated or deactivated) can be used to verify the non-linear sensor model.

The approximate linearity of the displacement readings may break down with changes in temperature. Accordingly, in one embodiment, the collimator 100 includes one or more heating elements (not shown) that heat portions of the collimator to a fixed temperature. In one embodiment, the displacement gauge 194 and analog components that control the displacement gauge 194 are heated. The heating elements may be attached to temperature controllers that maintain the displacement gauge 194 and its control circuitry at a fixed temperature that is above an operating temperature of the collimator 100. This ensures that readings of the displacement gauge 194 will not change due to changes in temperature during operation. In one embodiment, if the temperature varies from the fixed temperature by more than a threshold during operation, treatment is stopped.

In one embodiment, a temperature sensor is located at the displacement gauge 194 to monitor temperature of the displacement gauge 194. Additionally, temperature sensors may be positioned to measure temperatures of processing electronics (e.g., control circuitry) for signals from the displacement gauge 194. The temperature sensors may provide relative or absolute measures of temperature.

In one embodiment, a relationship between voltage output by the displacement gauge 194 and temperature is generated for each position (e.g., for the position of the first limit switch and the second limit switch, and the multiple positions for the intermediate limit switch). The sensor response model can be generated using two or more reference points (e.g., two or more temperatures).

In one embodiment, a sensor response model is built at one or more operating temperatures. Prior to using the variable aperture collimator 100 at a particular operating temperature, a sensor model (either linear or non-linear) is used to compute a sensor output value (of the displacement gauge) that corresponds to one of the positions of the intermediate aperture limit switch 193. An actual sensor reading at the limit switch position is then obtained and compared to the computed value. If the computed and actual readings agree within a tolerance limit (e.g., 0.1 mm), then the sensor model is validated at that operating temperature. Once the sensor model is validated at an operating temperature, the sensor model can be used to adjust the aperture of the variable aperture collimator 100 precisely. Note that if a sensor model has not been generated for a particular operating temperature, then a sensor model for that operating temperature may be derived by interpolation using sensor models at other operating temperatures.

Figure 6:
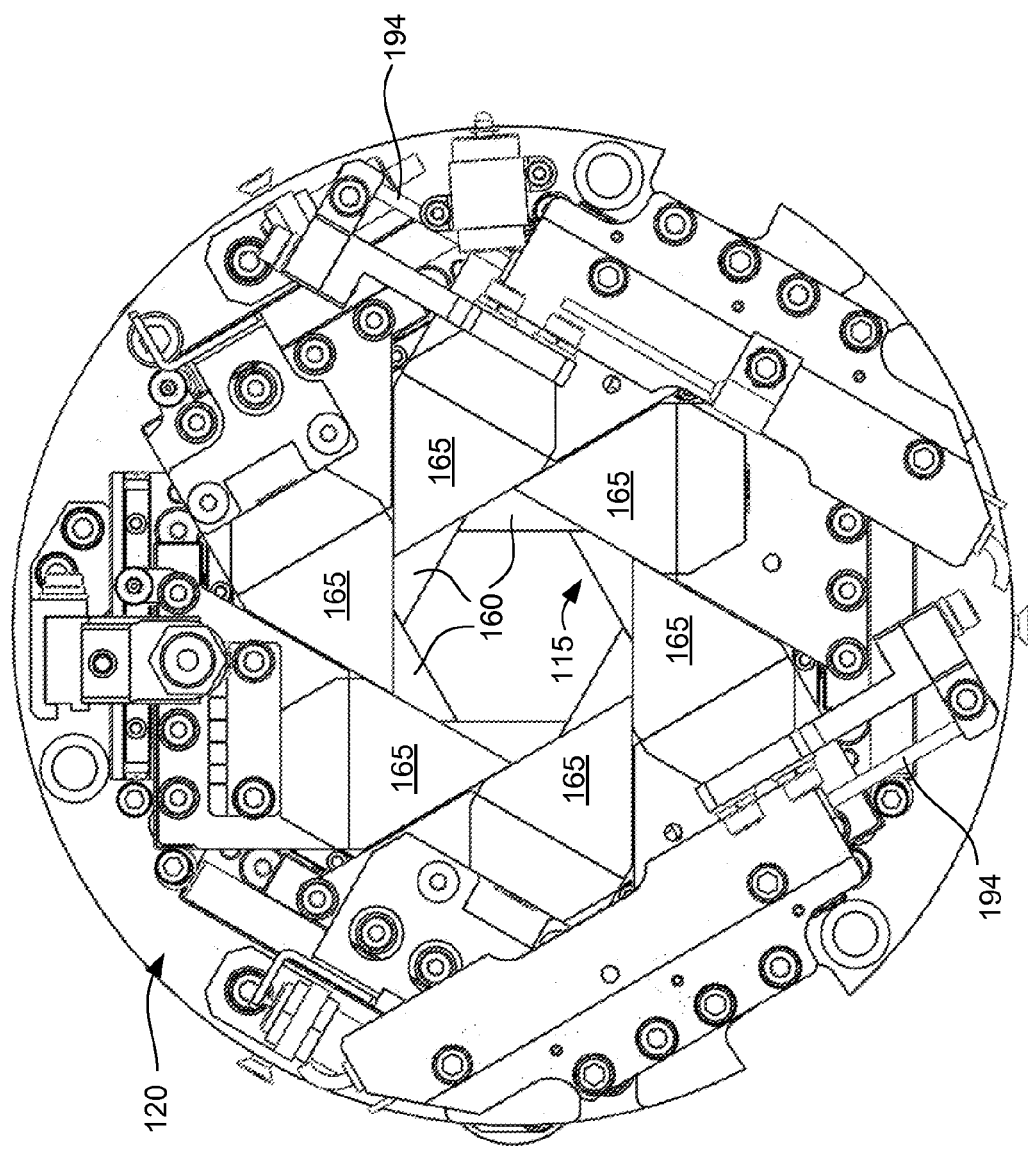
FIG. 6 illustrates a bottom view of a variable aperture collimator showing a bottom bank of collimation leaves and a partial view of a top bank of collimation leaves, in accordance with one embodiment of the present invention.

FIG. 6 illustrates a bottom view of the collimator 100 showing the bottom bank 120 and a partial view of the top bank 115, in accordance with one embodiment of the present invention. In one embodiment, the bottom bank 120 has a larger aperture than the top bank 115. Therefore, the top bank 115 and bottom bank 120 form a reverse funnel for treatment beams traveling through the collimator 100. In one embodiment, the bottom bank 120 is rotated a predetermined amount about the treatment axis with respect to the top bank 115. This ensures that any rays of radiation passing through gaps between the leaves in the top bank 115 are blocked by the leaves of the bottom bank 120. Additionally, by rotating the bottom bank 120 with respect to the top bank 115, the top and bottom banks combine to form a 12 sided polygon, which more closely approximates the shape of a circle. In one embodiment, the bottom bank is rotated 15 degrees or 30 degrees from the top bank. Therefore, the inner opening formed by the leaves 160, 165 may be a 12 sided regular polygon.

Figure 7:
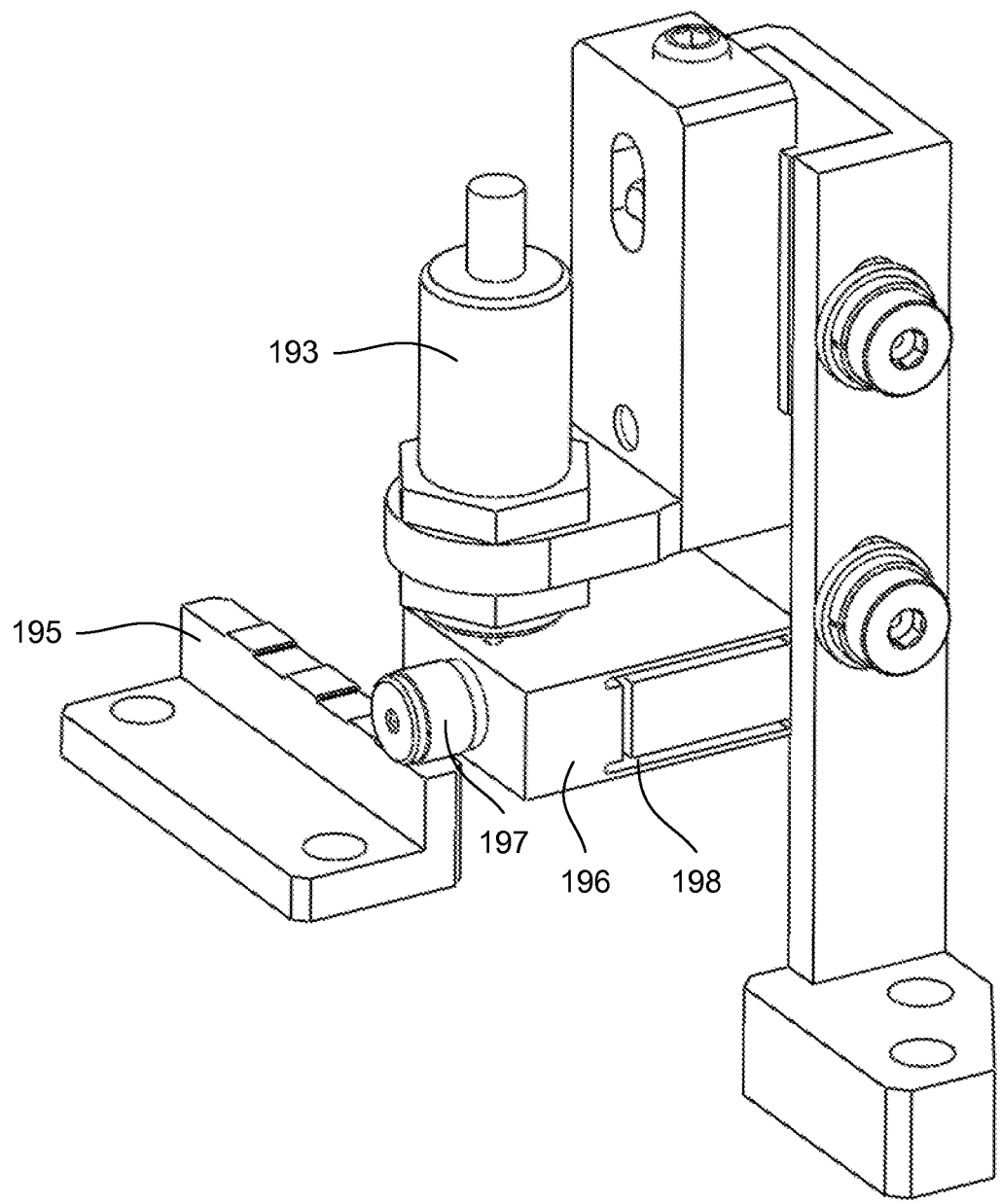
FIG. 7 illustrates a schematic diagram showing an intermediate aperture limit switch for a variable aperture collimator, in accordance with one embodiment of the present invention.

FIG. 7 illustrates a schematic diagram showing the intermediate aperture limit switch 193, in accordance with one embodiment of the present invention. In one embodiment, a carriage 195 is attached to a wing to which a leaf is affixed. As the aperture of the collimator is adjusted, the leaf is moved linearly along a guided path (e.g., by the cam plate and cam follower). Additionally, the carriage 195 is also moved linearly along the guided path. A bearing 197 attached to a flexure 196 rides the carriage 195. The carriage 195 includes a series of rises and dips. As the bearing 197 moves over a dip in the carriage 195, the flexure flexes away from the limit switch 193, thus deactivating the limit switch 193. As the bearing moves over a rise in the carriage 195, the flexure 196 flexes toward the limit switch 193, causing the limit switch 193 to be activated. In one embodiment, the flexure 196 includes a stop 198 that prevents over travel of the flexure 196. Therefore, the flexure 196 may not be stressed, prolonging the life span of the flexure 196. The flexure 196 provides very repeatable measurements without backlash or hysteresis. Alternatively, bearings or a plunger may be used to activate and deactivate the intermediate limit switch 193.

As discussed above, a displacement reading (e.g., a voltage) may be recorded each time the limit switch 193 is activated (e.g., each time the bearing 197 encounters a rise in the carriage) and each time the limit switch is deactivated e.g., each time the bearing 197 encounters a dip in the carriage). Therefore, three rises (as shown) may generate six readings.

In one embodiment, different displacement gauge values are measured depending on the direction of travel of a leaf. This may be caused, for example, by hysteresis. Therefore, three rises may generate 12 readings if readings are taken for both directions of movement (e.g., 6 readings generated during opening of the variable aperture collimator and 6 readings generated during closing of the variable aperture collimator).

In one embodiment, in addition to being used for calibration, the intermediate limit switch and carriage may be used to position the collimation leaves at predetermined positions (and thus to set the aperture of the variable aperture collimator to predetermined values). For example, it may be known that a first dip in the carriage corresponds to a first aperture of the variable aperture collimator, and that a second dip in the carriage corresponds to a second aperture of the variable aperture collimator. Thus, when the intermediate limit switch encounters the first dip, it may be confirmed that the variable aperture collimator has the first aperture, for example. Accordingly, if there are 12 intermediate positions detectable by the intermediate limit switch, an open position detectable by a first limit switch and a closed position detectable by a second limit switch, then the variable aperture collimator may be adjusted to 14 different known apertures based on the limit switches.

Figure 8A:
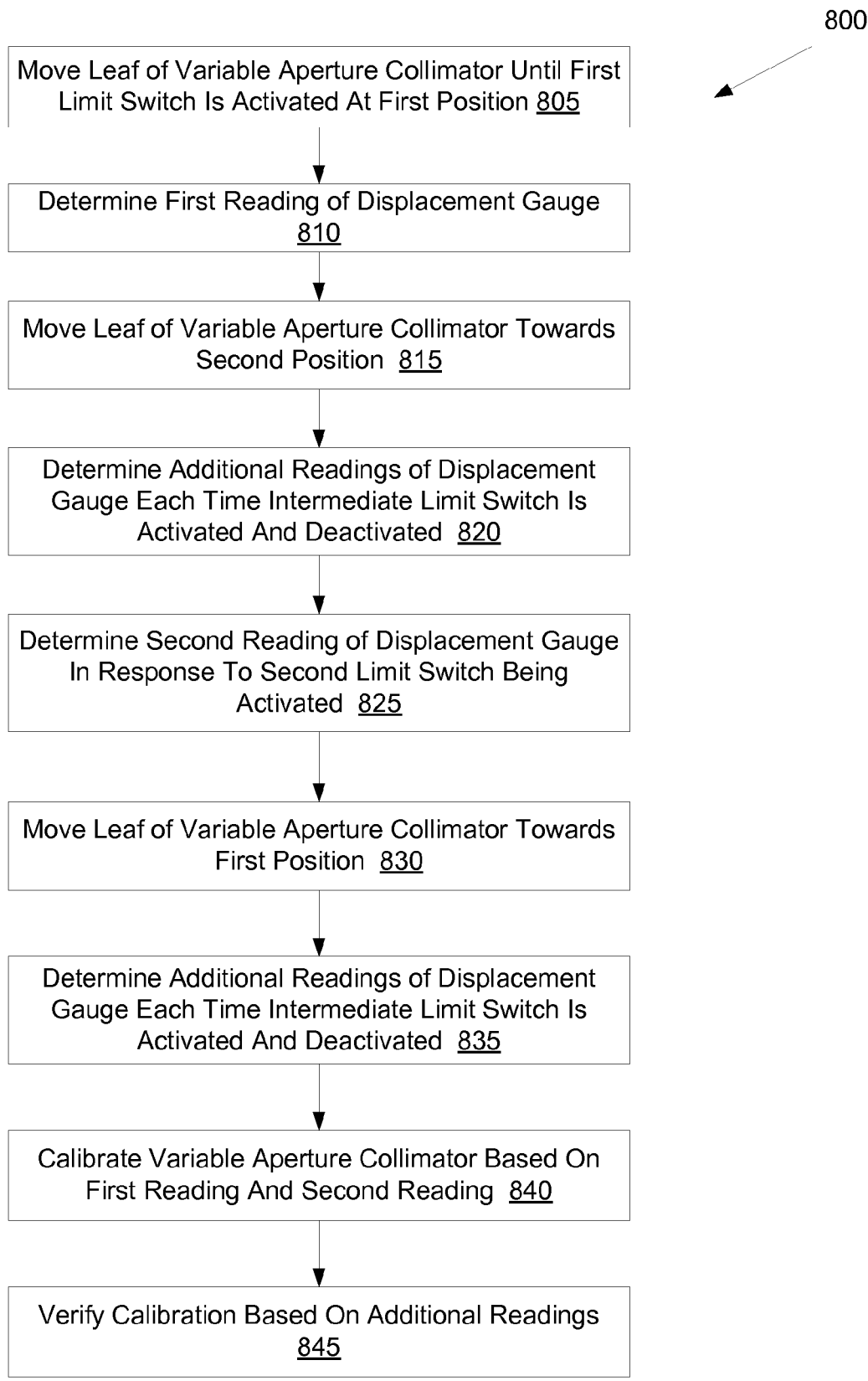
FIG. 8A illustrates a method of automatically calibrating an apparatus, in accordance with one embodiment of the present invention.

FIG. 8A illustrates a method 800 of automatically calibrating an apparatus, in accordance with one embodiment of the present invention. In one embodiment, method 800 is performed to calibrate a variable aperture collimator, such as variable aperture collimator 100. Alternatively, method 800 may be performed to automatically calibrate any apparatus having a portion that travels along a guided path that measures displacement or position. Method 800 will be discussed with reference to a variable aperture collimator. However, it should be understood that method 800 may also be used to calibrate other devices.

At block 805 of method 800, a variable aperture collimator moves a leaf (or multiple leaves) until a first limit switch is activated at a first position. The variable aperture collimator may move the leaf in response to a control signal received from a processing device. In one embodiment, the processing device corresponds to treatment delivery system 1115 of FIG. 11.

At block 810, the collimator determines a first reading of a displacement gauge and provides the first reading to the processing device. At block 815, the collimator moves the leaf towards a second position (e.g., based on a command received from the processing device). At block 820, the collimator determines additional readings of the displacement gauge each time an intermediate limit switch is activated or deactivated, and provides the additional readings to the processing device. At block 825, the collimator moves the leaf to the second position (e.g., based on a command received from the processing device), and determines a second reading of the displacement gauge in response to a second limit switch being activated. The collimator may send the second reading to the processing device. At block 830, the collimator moves the leaf back towards the first position. At block 835, the collimator determines additional readings of the displacement gauge each time the intermediate limit switch is activated or deactivated, and sends the additional readings to the processing device.

At block 840, the processing device calibrates the variable aperture collimator using the first reading and the second reading along with known apertures corresponding to the first reading and the second reading. At block 845, the processing device verifies the calibration of the collimator using the intermediate readings of the displacement gauge. At every calibration and verification, the relationship between aperture and displacement gauge readings is reestablished. The verification process guarantees that the positions of three or more limit switches as well as other parts of the overall assembly interfacing with these limit switches is constant, therefore ensuring unchanged apertures overall.

Figure 8B:
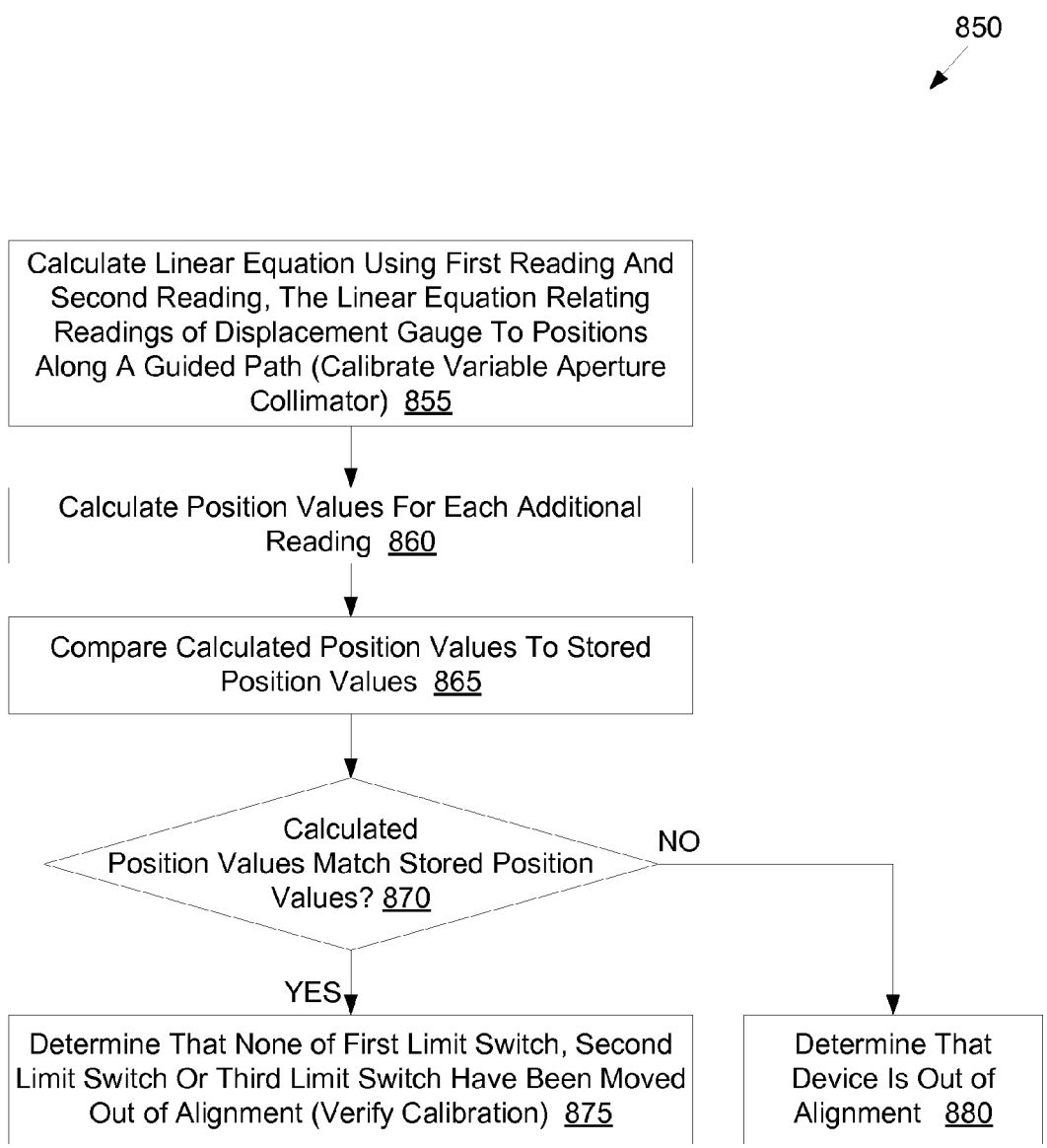
FIG. 8B illustrates another method of automatically calibrating an apparatus, in accordance with one embodiment of the present invention.

FIG. 8B illustrates another method 850 of automatically calibrating a variable aperture collimator, in accordance with one embodiment of the present invention. In one embodiment, method 850 corresponds to blocks 840 and 845 of method 800.

At block 855 of method 850, the processing device calculates a correlation factor using the first reading and the second reading, along with recorded values for apertures corresponding to the first reading and the second reading. In one embodiment, as shown, the correlation factor is a linear equation. Alternatively, the correlation factor may be a nonlinear equation. The first limit switch may be assumed to be positioned at a first known displacement, and the second limit switch may be assumed to be positioned at a second known displacement. These limit switches may have been positioned accurately during assembly (or a previous calibration) such that the aperture of the collimator is known at fully opened and fully closed positions. In one embodiment, the aperture fully closed position is approximately 0.0 mm+/−0.1 mm and the fully open position is 34 mm+/−0.1 mm. The correlation factor may be calculated (e.g., the linear equation may be solved) using the first assumed aperture, the first measured value, the second assumed aperture and the second measured value. The correlation factor (e.g., linear equation, nonlinear equation, etc.) relates readings of the displacement gauge to positions along the guided path and to apertures of the collimator. Therefore, any measured value of the displacement gauge can be inserted into the correlation factor to determine a displacement of the leaf, and thus the aperture of the collimator.

At block 860, the processing device uses the correlation factor and the intermediate readings of the displacement gauge to determine displacement positions and/or apertures (e.g., in mm) for each of the intermediate readings. At block 865, the processing device compares the calculated position values to stored position values. The stored position values may be stored in a calibration file that was generated during a previous calibration. The stored position values may have been generated based on displacement gauge readings during an initial calibration performed by a technician.

At block 870, the processing device determines whether the calculated position values match the stored position values. If the calculated position values match the stored position values, then the method proceeds to block 875. Otherwise, something may be mechanically wrong, and the method proceeds to block 880. Alternatively, if the calculated position values fail to match the stored position values, the method may return to block 855 and repeat the discussed operations using measurements of a redundant or backup intermediate limit switch. In another embodiment, methods 800 and/or 850 may be repeated using a secondary or redundant intermediate limit switch. In one embodiment, the calculated position values are considered to match the stored position values if 75% of the calculated values are within 0.1 mm of their stored counterparts.

At block 875, the processing device determines that none of the first limit switch, intermediate limit switch or third limit switch have been moved out of alignment. Therefore, the processing device verifies the calibration.

In one embodiment, at block 880, the processing device determines that the device is out of alignment, and that the calibration results are unreliable. The calculated positions may fail to match the stored positions if any of the limit switches has been jarred or moved since the initial calibration was performed.

Figure 9A:
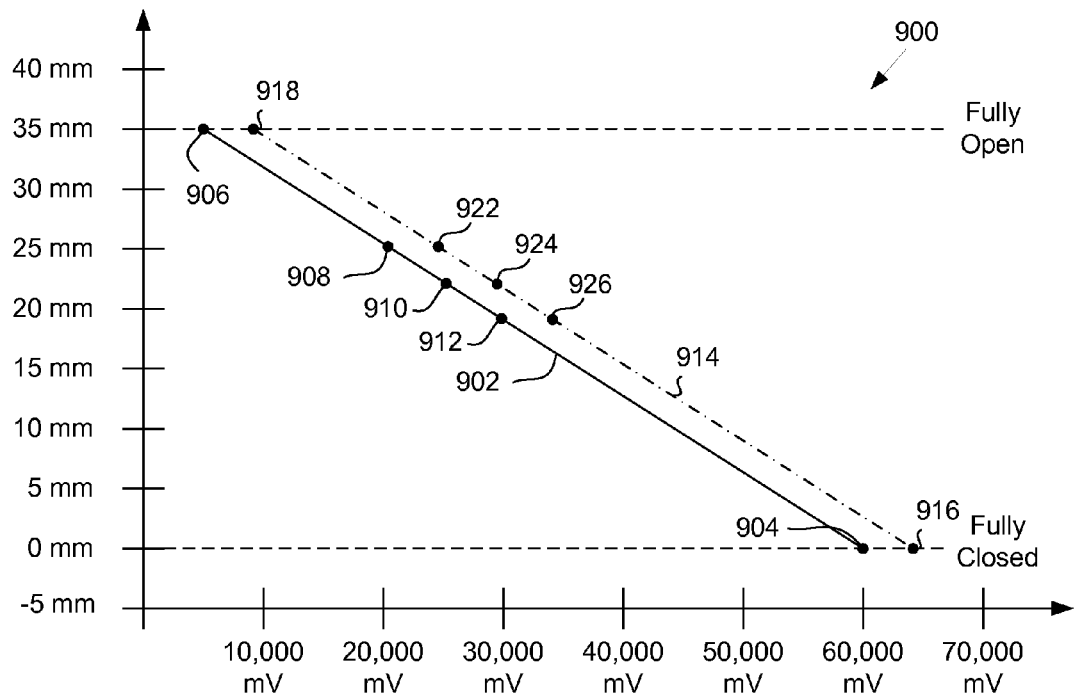
FIGS. 9A-9C are graphs showing calibration results, in accordance with embodiments of the present invention.
Figure 9B:
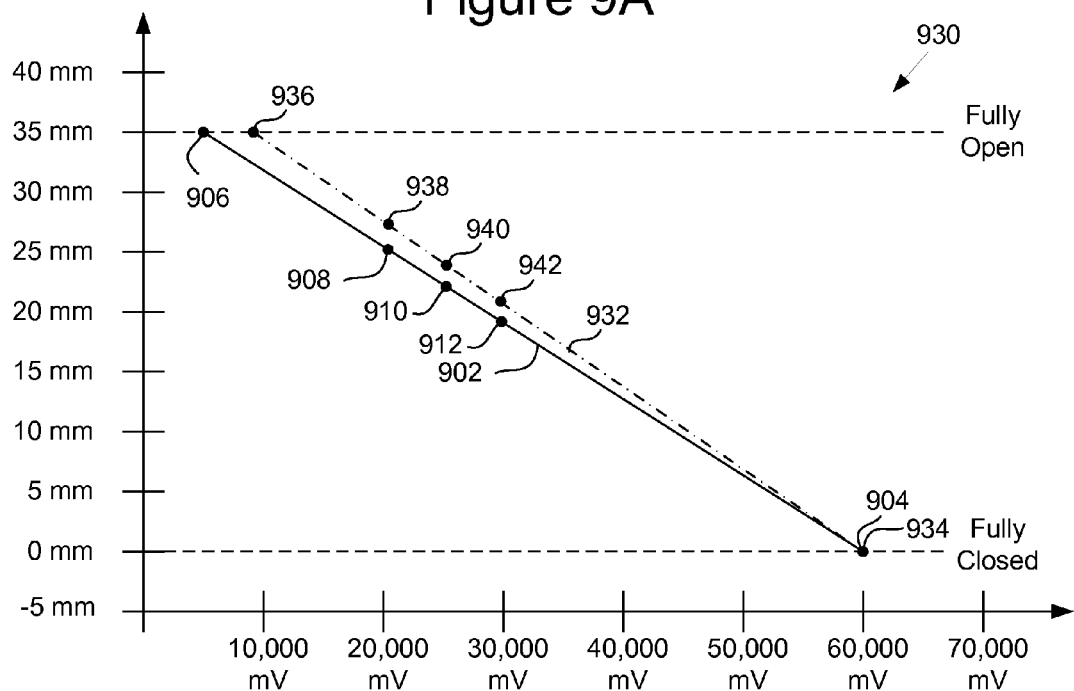
Figure 9C:
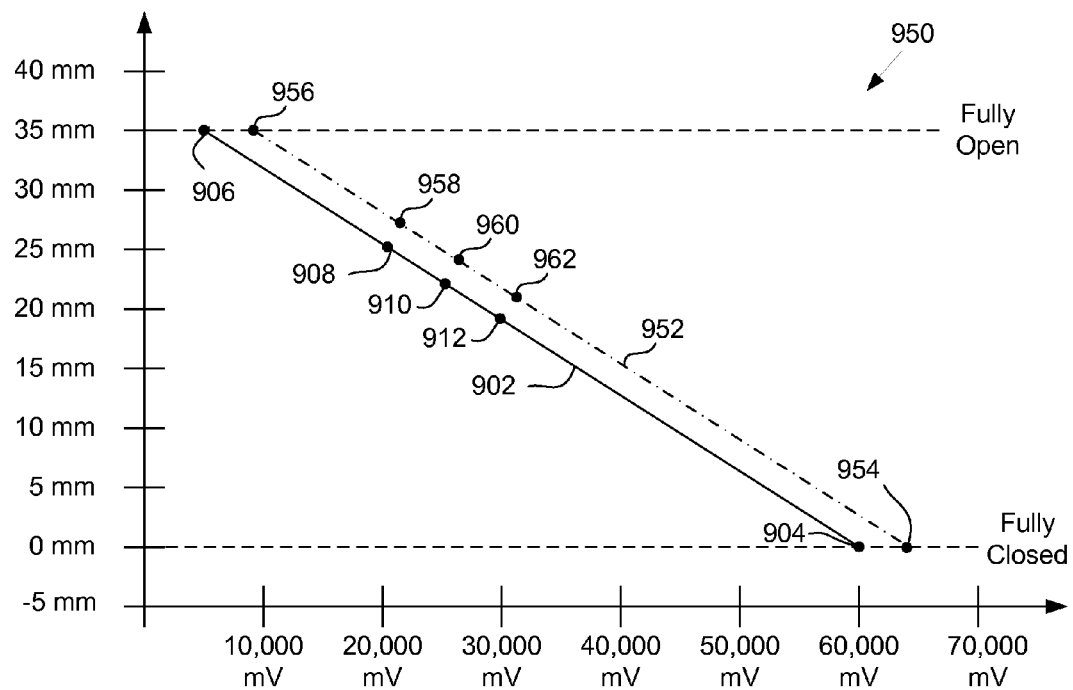

FIGS. 9A-9C illustrate graphs showing calibration results reflecting different circumstances, in accordance with embodiments of the present invention. Each graph shows collimator aperture (in mm) verses voltage (in mV). In each graph, a solid line 902 represents an initial calibration of a variable aperture collimator that may have been performed by a technician. Before the initial calibration was performed, a position of a first limit switch and a position of a second limit switch were verified. Therefore, it is known that the first limit switch will be activated when the variable aperture collimator is in a fully closed position with a known aperture, and that the second limit switch will be activated when the variable aperture collimator is in a fully open position. A first displacement reading 904 (measured in voltage) was then taken at the position at which the first limit switch was activated (at fully closed aperture) and a second displacement reading 906 was taken at the position at which the second limit switch was activated (at full open aperture). Additional displacement readings 908, 910, 912 were taken at intermediate positions at which an intermediate limit switch (or multiple intermediate limit switches) was activated and/or deactivated. Note that three intermediate positions are shown. However, more or fewer intermediate positions may be used. For example, as few as one or two, or as many as 12 or more intermediate positions may be used.

In one embodiment, the relationship between displacement (and therefore aperture) and voltage as measured by a displacement gauge is a nearly linear relationship. Accordingly, a linear equation can be computed based on the first reading 904 and the second reading 906 given the known positions of the first limit switch and the second limit switch. The positions at which the intermediate limit switch (or intermediate limit switches) were activated and/or deactivated can then be computed by finding apertures (in mm) that correspond to displacement readings (in mV) using the computed linear equation represented by line 902. The computed apertures corresponding to the positions of the intermediate limit switch are then stored.

There are numerous conditions that may cause calibration to change. These conditions are divided into mechanical changes and measurement response changes. Measurement response changes include drift in measurements caused by environmental conditions such as changes in temperature and drift in measurements caused by age of the sensor (e.g., due to mechanical wear, small changes in electrical properties, radiation effects on components, etc.). Mechanical changes include changes in position of one or more of the limit switches, components connected to limit switches, the displacement gauge, or assemblies for these components. Measurement response changes can be corrected by automatically recalibrating the collimator before each treatment session. As part of verification of recalibration, an external measurement may be taken to ensure current aperture values are consistent with previous aperture values. If the external measurement fails (implying a mechanical change), then the collimator may need to be manually recalibrated. Manual recalibration may include physically repositioning one or more of the limit switches.

FIG. 9A is a graph 900 showing calibration results with measurement response changes. A dashed line 904 represents an automatic calibration performed for a variable aperture collimator. To perform the calibration, a first displacement measurement 916 is recorded at the first limit switch, a second displacement measurement 918 is recorded at the second limit switch, and the intermediate displacement measurements are recorded based on the intermediate limit switch activation and/or deactivation positions. The same number of intermediate displacement measurements are taken during the automatic calibration as were taken during the initial calibration. A linear equation (or other correlation factor) for the dashed line 914 is then computed using the first displacement measurement 916 and the second displacement measurement 918 along with assumed apertures for the first measurement 916 and the second measurement 918. The intermediate displacement measurements 922, 924, 926 are then inserted into the linear equation (or other correlation factor) to solve for the collimator apertures corresponding to those displacement measurements. As illustrated, the computed collimator apertures for the intermediate positions are unchanged from the initial calibration, even though the displacement readings were different. Since the computed intermediate apertures match the stored intermediate apertures 908, 910, 912, the calibration is verified.

FIG. 9B is a graph 930 showing calibration results after the first limit switch has been moved out of alignment. A dashed line 932 represents an automatic calibration performed for the variable aperture collimator. To perform the calibration, a first displacement measurement 934 is recorded at the first limit switch, a second displacement measurement 936 is recorded at the second limit switch, and the intermediate displacement measurements 938, 940, 942 are recorded based on the intermediate limit switch activation and/or deactivation positions. A linear equation (or other correlation factor) for the dashed line 932 is then computed using the first displacement measurement 934 and the second displacement measurement 936 along with the known maximum and minimum apertures. The intermediate displacement measurements 938, 940, 942 are then plugged into the linear equation (or other correlation factor) to solve for the apertures corresponding to those displacement measurements. As illustrated, intermediate readings 938, 940 and 942 and the first reading 934 are unchanged from the initial calibration. However, the second reading 936 is different. This indicates that the second limit switch has been moved. Even though the intermediate readings 938, 940, 942 are unchanged, they now correspond to different apertures when they are fit to line 932. Therefore, the calibration results fail verification.

FIG. 9C is a graph 950 showing calibration results after the intermediate limit switch has been moved out of alignment. A dashed line 952 represents an automatic calibration performed for the variable aperture collimator. To perform the calibration, a first displacement measurement 954 is recorded at the first limit switch, a second displacement measurement 956 is recorded at the second limit switch, and the intermediate displacement measurements 958, 960, 962 are recorded based on the intermediate limit switch activation and/or deactivation positions. A linear equation (or other correlation factor) for the dashed line 952 is then computed using the first displacement measurement 934 and the second displacement measurement 936 along with the known maximum and minimum apertures. As shown, the line 952 is shifted, but the slope is unchanged. This indicates that the first limit switch and second limit switch are aligned, and that measurement drift has occurred since the initial calibration. The intermediate displacement measurements 958, 960, 962 are then plugged into the linear equation (or other correlation factor) to solve for the apertures corresponding to those displacement measurements. As illustrated, intermediate readings 958, 960 and 962 all have different displacement values than in the initial calibration. This may indicate that a position of the intermediate limit switch has changed (it has been moved out of alignment). Therefore, the calibration results may fail verification.

Figure 10:
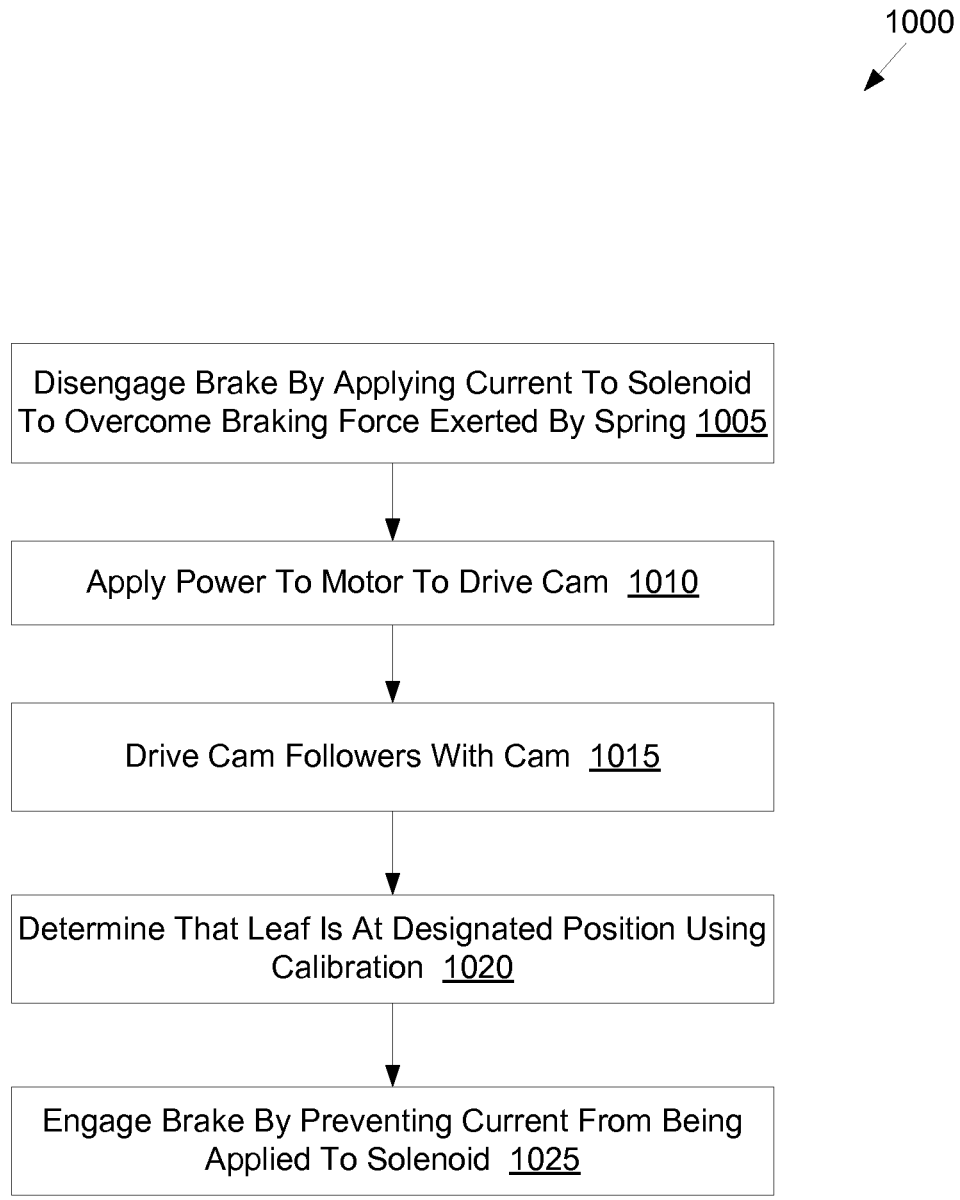
FIG. 10 illustrates a flow diagram for a method of braking a variable aperture collimator, in accordance with one embodiment of the present invention.

FIG. 10 illustrates a method 1000 of braking a variable aperture collimator, in accordance with one embodiment of the present invention. In one embodiment, method 1000 is performed by a variable aperture collimator and/or a processing device connected with the variable aperture collimator. The processing device may send control signals to the variable aperture collimator, and may receive sensor readings from the variable aperture collimator. At block 1005 of method 1000, the variable aperture collimator disengages a brake by applying current to a solenoid to overcome a braking force exerted by a spring. At block 1010, the variable aperture collimator applies power to a motor to drive a cam plate. At block 1015, as the cam plate rotates, the cam plate drives multiple cam followers. At block 1020, the variable aperture collimator determines that one or more collimation leaves are at a designated position. The variable aperture collimator may use calibration results that were previously generated (e.g., as described above with reference to methods 800 and 850) to determine when the leaf is at the designated location. The variable aperture collimator then engages the brake by preventing current from being applied to the solenoid. When the solenoid is deactivated, the force applied by the springs engages the brake, thus ensuring that the leaves will not move out of position.

Figure 11:
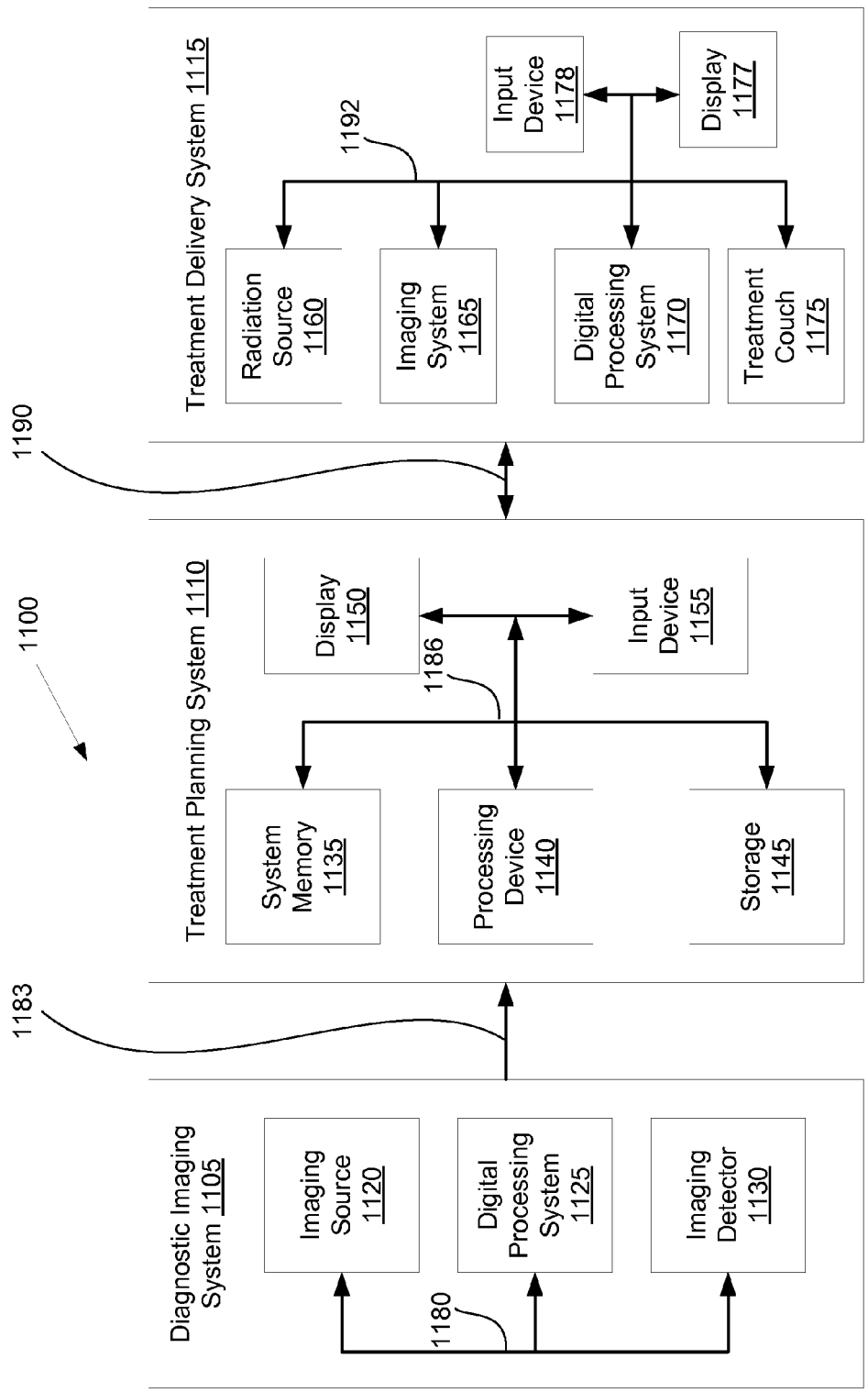
FIG. 11 illustrates one embodiment of systems that may be used in performing radiation treatment.

FIG. 11 illustrates one embodiment of systems that may be used in generating a treatment plan and/or performing radiation treatment. Radiation treatment includes both radiation surgery (radiosurgery) and radiation therapy (radiotherapy). Radiotherapy and radiosurgery differ in the amount of radiation delivered to a patient in a treatment session. The amount of radiation in an individual session or fraction utilized in radiotherapy treatment sessions is typically about an order of magnitude smaller, as compared to the amount used in a radiosurgery session. For convenience, the term "radiation treatment" is used herein to mean radiosurgery and/or radiotherapy unless otherwise noted by the magnitude of the radiation.

These systems may be used to perform, for example, the methods described above. As described below and illustrated in FIG. 11, a system 1100 may include a diagnostic imaging system 1105, a treatment planning system 1110, a treatment delivery system 1115 and a motion detecting system (not shown). In one embodiment, the diagnostic imaging system 1105 and the motion detecting system are combined into a single unit.

Diagnostic imaging system 1105 may be any system capable of producing medical diagnostic images of a patient that may be used for subsequent medical diagnosis, treatment planning, treatment simulation and/or treatment delivery. For example, diagnostic imaging system 1105 may be a computed tomography (CT) system, a magnetic resonance imaging (MRI) system, a positron emission tomography (PET) system, or the like. For ease of discussion, diagnostic imaging system 1105 may be discussed below at times in relation to an x-ray imaging modality. However, other imaging modalities such as those above may also be used.

In one embodiment, diagnostic imaging system 1105 includes an imaging source 1120 to generate an imaging beam (e.g., x-rays) and an imaging detector 1130 to detect and receive the beam generated by imaging source 1120, or a secondary beam or emission stimulated by the beam from the imaging source (e.g., in an MRI or PET scan).

The imaging source 1120 and the imaging detector 1130 may be coupled to a digital processing system 1125 to control the imaging operation and process image data. In one embodiment, diagnostic imaging system 1105. In another embodiment, diagnostic imaging system 1105 may receive imaging commands from treatment delivery system 1115.

Diagnostic imaging system 1105 includes a bus or other means 1180 for transferring data and commands among digital processing system 1125, imaging source 1120 and imaging detector 1130. Digital processing system 1125 may include one or more general-purpose processors (e.g., a microprocessor), special purpose processor such as a digital signal processor (DSP) or other type of device such as a controller or field programmable gate array (FPGA). Digital processing system 1125 may also include other components (not shown) such as memory, storage devices, network adapters and the like. Digital processing system 1125 may be configured to generate digital diagnostic images in a standard format, such as the DICOM (Digital Imaging and Communications in Medicine) format, for example. In other embodiments, digital processing system 1125 may generate other standard or non-standard digital image formats. Digital processing system 1125 may transmit diagnostic image files (e.g., the aforementioned DICOM formatted files) to treatment delivery system 1115 over a data link 1183, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treat a patient despite the existence of a physical separation between the system user and the patient.

Treatment delivery system 1115 includes a therapeutic and/or surgical radiation source 1160 to administer a prescribed radiation dose to a target volume in conformance with a treatment plan. Treatment delivery system 1115 may also include a digital processing system 1170 to control radiation source 1160, receive and process data from diagnostic imaging system 1105 and/or motion detecting system 1106, control a patient support device such as a treatment couch 1175, and control a variable aperture collimator. Digital processing system 1170 may include one or more general-purpose processors (e.g., a microprocessor), special purpose processor such as a digital signal processor (DSP) or other type of device such as a controller or field programmable gate array (FPGA). Digital processing system 1170 may also include other components (not shown) such as memory, storage devices, network adapters and the like.

In one embodiment, digital processing system 1170 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 1170 may also include a storage device, representing one or more storage devices (e.g., a magnetic disk drive or optical disk drive) for storing information and instructions. The storage device may be used for storing instructions for performing the treatment delivery steps discussed herein. Digital processing system 1170 may be coupled to radiation source 1160 and treatment couch 1175 and/or a variable aperture collimator by a bus 1192 or other type of control and communication interface.

Digital processing system 1170 may implement methods to calibrate and control a variable aperture collimator, and to control a shape and size of a radiation treatment beam delivered by the radiation source 1160 using the variable aperture collimator. Controlling the variable aperture collimator may include adjusting an aperture of the variable aperture collimator. In one embodiment, the digital processing system 1170 executes a calibration function before beginning radiation treatment to calibrate the variable aperture collimator. The processing system 1170 may drive a motor of the variable aperture collimator, receive signals from limit switches and receive measurement data from displacement gauges included in the variable aperture collimator. Processing system 1170 may use this data to automatically calibrate the variable aperture collimator.

Treatment delivery system 1115 may include an imaging system 1165 to image a target. In one embodiment, the treatment delivery system 1115 includes an input device 1178 and a display 1177 connected with digital processing system 1170 via bus 1192. The display 1177 can show trend data that identifies a rate of target movement (e.g., a rate of movement of a target volume that is under treatment). The display can also show a current radiation exposure of a patient and a projected radiation exposure for the patient. The input device 1178 can enable a clinician to adjust parameters of a treatment delivery plan during treatment.

Treatment planning system 1110 includes a processing device 1140 to generate and modify treatment plans and/or simulation plans. Processing device 1140 may represent one or more general-purpose processors (e.g., a microprocessor), special purpose processor such as a digital signal processor (DSP) or other type of device such as a controller or field programmable gate array (FPGA). Processing device 1140 may be configured to execute instructions for treatment planning operations.

Treatment planning system 1110 may also include system memory 1135 that may include a random access memory (RAM), or other dynamic storage devices, coupled to processing device 1140 by bus 1186, for storing information and instructions to be executed by processing device 1140. System memory 1135 also may be used for storing temporary variables or other intermediate information during execution of instructions by processing device 1140. System memory 1135 may also include a read only memory (ROM) and/or other static storage device coupled to bus 1186 for storing static information and instructions for processing device 1140.

Treatment planning system 1110 may also include storage device 1145, representing one or more storage devices (e.g., a magnetic disk drive or optical disk drive) coupled to bus 1186 for storing information and instructions. Storage device 1145 may be used for storing instructions for performing the treatment planning steps.

Processing device 1140 may also be coupled to a display device 1150, such as a cathode ray tube (CRT) or liquid crystal display (LCD), for displaying information (e.g., a 2D or 3D representation of the VOI) to the user. An input device 1155, such as a keyboard, may be coupled to processing device 1140 for communicating information and/or command selections to processing device 1140. One or more other user input devices (e.g., a mouse, a trackball or cursor direction keys) may also be used to communicate directional information, to select commands for processing device 1140 and to control cursor movements on display 1150.

Treatment planning system 1110 may share its database (e.g., data stored in storage 1145) with a treatment delivery system, such as treatment delivery system 1115, so that it may not be necessary to export from the treatment planning system prior to treatment delivery. Treatment planning system 1110 may be linked to treatment delivery system 1115 via a data link 1190, which may be a direct link, a LAN link or a WAN link.

It should be noted that when data links 1183 and 1190 are implemented as LAN or WAN connections, any of diagnostic imaging system 1105, treatment planning system 1110 and/or treatment delivery system 1115 may be in decentralized locations such that the systems may be physically remote from each other. Alternatively, any of diagnostic imaging system 1105, treatment planning system 1110, and/or treatment delivery system 1115 may be integrated with each other in one or more systems.

Figure 12:
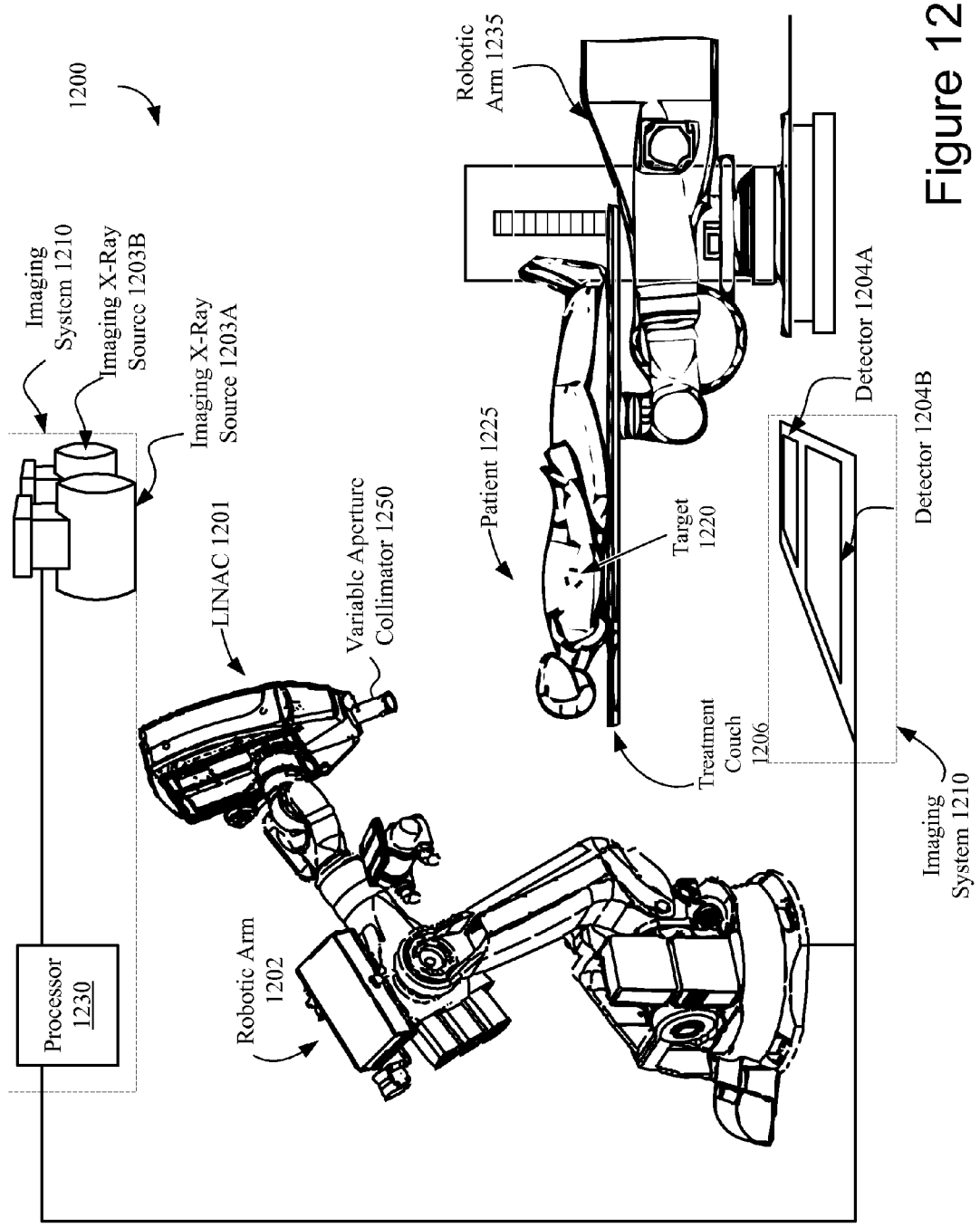
FIG. 12 illustrates a configuration of an image-guided radiation treatment system, in accordance with embodiments of the present invention.

FIG. 12 illustrates a configuration of an image-guided radiation treatment system 1200, in accordance with one embodiment of the present invention. In the illustrated embodiment, the radiation treatment system 1200 includes a linear accelerator (LINAC) 1201 that acts as a radiation treatment source. The LINAC 1201 is mounted on the end of a robotic arm 1202 having multiple (e.g., 5 or more) degrees of freedom in order to position the LINAC 1201 to irradiate a pathological anatomy (e.g., target 1220) with beams delivered from many angles, in many planes, with many beam shapes and/or sizes, in an operating volume around a patient 1225. In one embodiment, a variable aperture collimator 1250 (which may correspond to variable aperture collimator 100) is mounted to a front of the LINAC 1201. Treatment may involve beam paths with a single isocenter, multiple isocenters, or with a non-isocentric approach. Alternatively, other types of image guided radiation treatment (IGRT) systems may be used. In one alternative embodiment, the LINAC 1201 may be mounted on a gantry based system to provide isocentric beam paths. In one particular embodiment, the IGRT system is the Vero SBRT System (referred to as TM200 in Japan), a joint product of Mitsubishi Heavy Industries Ltd., of Tokyo Japan and BrainLAB AG of Germany, that utilizes a rigid O-ring based gantry. Such an O-ring based gantry system is described in greater detail below with reference to FIG. 13.

The LINAC 1201 may be positioned at multiple different nodes (predefined positions at which the robot stops and radiation may be delivered) during treatment by moving the robotic arm 1202. At the nodes, the LINAC 1201 can deliver one or more radiation treatment beams to a target. Each treatment beam may be delivered with different aperture settings of the variable aperture collimator 1250. The nodes may be arranged in an approximately spherical distribution about a patient. The particular number of nodes and the number of treatment beams applied at each node may vary as a function of the location and type of pathological anatomy to be treated. For example, the number of nodes may vary from 50 to 300, or more preferably 15 to 100 nodes and the number of beams may vary from 1200 to 3200, or more preferably 50 to 300.

Radiation treatment system 1200, in accordance with one embodiment of the present invention, includes an imaging system 1210 having a processor 1230 connected with x-ray sources 1203A and 1203B and fixed x-ray detectors 1204A and 1204B. Alternatively, the x-ray sources 1203A, 1203B and/or x-ray detectors 1204A, 1204B may be mobile, in which case they may be repositioned to maintain alignment with the target 1220, or alternatively to image the target from different orientations or to acquire many x-ray images and reconstruct a three-dimensional (3D) cone-beam CT. In one embodiment the x-ray sources are not point sources, but rather x-ray source arrays, as would be appreciated by the skilled artisan. In one embodiment, LINAC 1201 serves as an imaging source (whether gantry or robot mounted), where the LINAC power level is reduced to acceptable levels for imaging.

Imaging system 1210 may perform computed tomography (CT) such as cone beam CT, and images generated by imaging system 1201 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment a robotic arm 1235 is used for positioning the patient. Imaging system 1210, thus, provides stereoscopic imaging of the target 1220 and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

Figure 13:
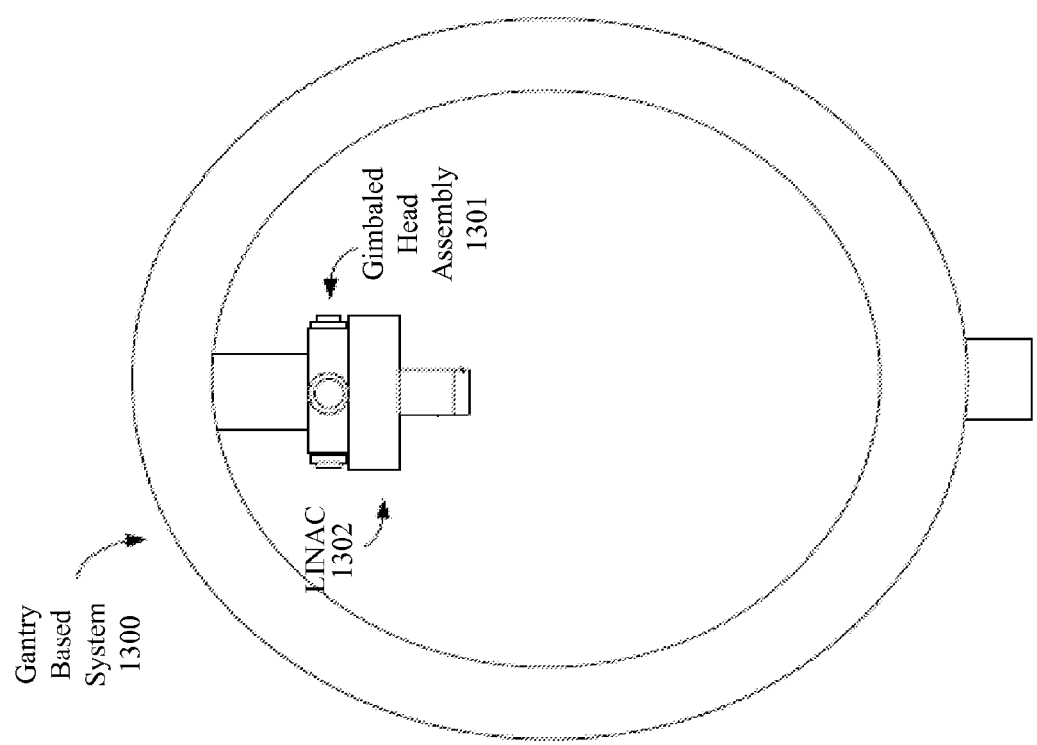
FIG. 13 illustrates a gantry based image-guided radiation treatment system, in accordance with embodiments of the present invention.

FIG. 13 illustrates one embodiment of a gantry based (isocentric) intensity modulated radiotherapy (IMRT) system 1300. In a gantry based system 1300, a radiation source (e.g., a LINAC) 1302 is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator (MLC) that allows portions of the beam to be blocked, so that the remaining beam incident on the patient has a pre-defined shape. The resulting system generates arbitrarily shaped radiation beams that intersect each other at the isocenter to deliver a dose distribution to the target. In one embodiment, the methods of calibration described herein are performed for the MLC. In one embodiment, calibration is performed separately for each independent movable leaf of the MLC.

In one embodiment, the gantry based system 1300 is an o-ring based system having a gimbaled radiation source head assembly 1301. The o-ring can be skewed around its vertical axis, and the gimbals can be driven to rotate in pan and tilt directions in order to position the linear accelerator 1302. In one embodiment, the gantry rotates 360 degrees about a horizontal axis, and additionally allows rotation about a vertical axis (a so called skew) of +/−60 degrees. Orthogonal gimbals hold the LINAC 1302, which allows pan and tilt motions of the LINAC. This system may include dual orthogonal imaging systems at 45 degrees from the treatment beam, to allow for the acquisition of x-ray images.

It will be apparent from the foregoing description that aspects of the present invention may be embodied, at least in part, in software. That is, the techniques may be carried out in a computer system or other data processing system in response to its processor, such as digital processing system 1170, for example, executing sequences of instructions contained in a memory. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as digital processing system 1170.

A machine-readable medium can be used to store software and data which when executed by a general purpose or special purpose data processing system causes the system to perform various methods of the present invention. This executable software and data may be stored in various places including, for example, system memory and storage or any other device that is capable of storing software programs and/or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc.

Unless stated otherwise as apparent from the foregoing discussion, it will be appreciated that terms such as "processing," "computing," "generating," "comparing" "determining," "calculating," "testing," "identifying," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Embodiments of the present invention are discussed with reference to variable aperture collimators. However, it should be understood that embodiments of the present invention may also apply to other types of devices. For example, embodiments of the present invention may apply to manufacturing machines, or any other devices for which accurate positioning is important. Therefore, embodiments of the present invention are not limited to variable aperture collimators or to the field of radiation treatment.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A variable aperture collimator comprising:
   at least one leaf that moves along a guided path, wherein movement of the at least one leaf along the guided path causes an aperture of the variable aperture collimator to change;
   a displacement gauge that outputs readings based on the at least one leaf's position on the guided path;
   an intermediate limit switch that is activated in response to the at least one leaf being moved to an intermediate position on the guided path; and
   a processing device to:
      calibrate the apparatus based on a first reading corresponding to a first position on the guided path and a second reading corresponding to a second position on the guided path, the first position corresponding to a minimum aperture of the variable aperture collimator and the second position corresponding to a maximum aperture of the variable aperture collimator; and
      verify the calibration based on a third reading corresponding to the intermediate position, wherein the third reading was generated in response to the intermediate limit switch being activated.

2. The variable aperture collimator of claim 1, further comprising:
   a first limit switch that is activated in response to the at least one leaf being moved to the first position on the guided path; and
   a second limit switch that is activated in response to the at least one leaf being moved to the second position on the guided path;
   wherein the processing device is to receive, from the displacement gauge, the first reading corresponding to the first position in response to the first limit switch being activated, the second reading corresponding to the second position in response to the second limit switch being activated and the third reading corresponding to the intermediate position in response to the intermediate limit switch being activated, wherein the intermediate position is between the first position and the second position.

3. The variable aperture collimator of claim 1, wherein to calibrate the variable aperture collimator the processing device calculates a linear equation using the first reading and the second reading, the linear equation relating readings of the displacement gauge to positions along the guided path.

4. The apparatus variable aperture collimator of claim 3, wherein to verify the calibration the processing device performs the following:
   calculates a current intermediate position value based on applying the third reading of the displacement gauge to the linear equation;
   compares the current intermediate position value to a stored intermediate position value; and
   determines that none of a first limit switch, a second limit switch or the third limit switch has been moved out of alignment if the current intermediate position value matches the stored intermediate position value.

5. The variable aperture collimator of claim 3, further comprising:
   a carriage attached to the at least one leaf, the carriage having a plurality of rises, wherein each of the plurality of rises causes the intermediate limit switch to be activated at the intermediate position or at an additional position of the at least one leaf on the guided path;
   wherein the processing device to:
      receive one or more additional readings of the displacement gauge in response to the intermediate limit switch being activated at additional positions along the guided path;
      calculate current values for the intermediate position and the one or more additional positions based on applying the third reading and the additional readings of the displacement gauge to the linear equation;
      compare the current intermediate position value to a stored intermediate position value and the current additional position values to stored additional position values; and
      verify the calibration if the current intermediate position value matches the stored intermediate position value and the current additional position values match the stored additional position values.

6. The variable aperture collimator of claim 5, further comprising:
   a flexure that rides the carriage, wherein the flexure flexes when the flexure encounters each of the plurality of rises, and wherein the intermediate limit switch is activated in response to the flexure flexing.

7. The variable aperture collimator of claim 1, wherein the displacement gauge is one of a linear displacement gauge or an angular displacement gauge.

8. The variable aperture collimator of claim 1, wherein the intermediate limit switch is one of a mechanical limit switch, a magnetic proximity switch or an optical proximity switch.

9. The variable aperture collimator of claim 1, wherein to calibrate the variable aperture collimator the processing device generates a non-linear sensor model relating readings of the displacement gauge to positions along the guided path, wherein the non-linear sensor model is generated using the first reading, the second reading and a fourth reading corresponding to an additional intermediate position, wherein the fourth reading was generated in response to the intermediate limit switch being activated.

10. A method of calibrating a variable aperture collimator having at least one leaf that moves along a guided path, comprising:
    calculating, by a processing device, a correlation factor using a first reading generated by a displacement gauge at a first position on the guided path and a second reading generated by the displacement gauge at a second position on the guided path, wherein the correlation factor relates readings of the displacement gauge to positions on the guided path, and wherein the first position corresponds to a minimum aperture of the variable aperture collimator and the second position corresponds to a maximum aperture of the variable aperture collimator;
    calculating, by the processing device, a current third position value based on applying a third reading of the displacement gauge to the correlation factor, wherein the third reading was generated by the displacement gauge in response to an intermediate limit switch being activated at an intermediate position on the guided path;
    comparing, by the processing device, the current third position value to a stored third position value; and determining, by the processing device, that the device is properly calibrated if the current third position value matches the stored third position value.

11. The method of claim 10, further comprising:

determining the first reading of the displacement gauge in response to a first limit switch being activated, wherein the first limit switch is activated as a result of the at least one leaf moving on the guided path to the first position;

determining the second reading of the displacement gauge in response to a second limit switch being activated, wherein the second limit switch is activated as a result of the at least one leaf moving on the guided path to the second position; and determining the third reading of the displacement gauge in response to the intermediate limit switch being activated at the intermediate position, wherein the intermediate position is between the first position and the second position.

12. The method of claim 10, further comprising:

determining one or more additional readings of the displacement gauge in response to the intermediate limit switch being activated or deactivated at additional positions on the guided path;

calculating current values for the additional positions based on applying the additional readings of the displacement gauge to the correlation factor;

comparing the current additional position values to stored additional position values; and determining that the device is properly calibrated if the current additional position values match the stored additional position values.

13. The method of claim 10, further comprising:

determining that the device is out of calibration when the current third position value fails to match the stored third position value.

* * * * *